US011452992B2

(12) United States Patent
Shaikh et al.

(10) Patent No.: US 11,452,992 B2
(45) Date of Patent: Sep. 27, 2022

(54) IRON OXIDE SUPPORTED RHODIUM CATALYST FOR NITROARENE REDUCTION

(71) Applicant: King Fahd University of Petroleum and Minerals, Dhahran (SA)

(72) Inventors: M. Nasiruzzaman Shaikh, Dhahran (SA); Md. Abdul Aziz, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 16/359,409

(22) Filed: Mar. 20, 2019

(65) Prior Publication Data

US 2020/0298212 A1  Sep. 24, 2020

(51) Int. Cl.
| | | |
|---|---|---|
| *B01J 23/46* | (2006.01) | |
| *B01J 35/00* | (2006.01) | |
| *B01J 35/08* | (2006.01) | |
| *B01J 35/10* | (2006.01) | |
| *B01J 37/02* | (2006.01) | |
| *B01J 37/08* | (2006.01) | |
| *B01J 35/02* | (2006.01) | |
| *C07C 209/32* | (2006.01) | |
| *B01J 23/745* | (2006.01) | |
| *C07C 211/45* | (2006.01) | |
| *C07C 211/50* | (2006.01) | |

(52) U.S. Cl.
CPC ......... *B01J 23/464* (2013.01); *B01J 35/0033* (2013.01); *B01J 35/023* (2013.01); *B01J 35/08* (2013.01); *B01J 35/1019* (2013.01); *B01J 37/0209* (2013.01); *B01J 37/08* (2013.01); *C07C 209/32* (2013.01); *B01J 23/745* (2013.01); *C07C 211/45* (2013.01); *C07C 211/50* (2013.01)

(58) Field of Classification Search
CPC ... B01J 23/464; B01J 23/8906; B01J 35/0033
See application file for complete search history.

(56) References Cited

U.S. PATENT DOCUMENTS 6,258,982 B1   7/2001  Baumeister et al.
2019/0382537 A1* 12/2019  Yamamoto ............ C07C 251/24

FOREIGN PATENT DOCUMENTS

| CN | 1272308 C | | 8/2006 |
|---|---|---|---|
| CN | 101767018 A | * | 7/2010 |
| CN | 105985248 A | | 10/2016 |

(Continued)

OTHER PUBLICATIONS

Machine translatin of JP2017-087151A, publication date May 2017.*

(Continued)

*Primary Examiner* — Jun Li
(74) *Attorney, Agent, or Firm* — Oblon, McClelland, Maier & Neustadt, L.L.P.

(57) ABSTRACT

A supported catalyst having rhodium particles with an average diameter of less than 1 nm disposed on a support material containing magnetic iron oxide (e.g. $Fe_3O_4$). A method of producing the supported catalyst and a process of reducing nitroarenes to corresponding aromatic amines employing the supported catalyst with a high product yield are also described. The supported catalyst may be recovered with ease using an external magnet and reused.

10 Claims, 41 Drawing Sheets

(56) References Cited

FOREIGN PATENT DOCUMENTS

| CN | 106800493 A | | 6/2017 |
|---|---|---|---|
| EP | 0 842 920 A2 | | 5/1998 |
| JP | 2017087151 A | * | 5/2017 |
| WO | 2007/116111 A1 | | 10/2007 |

OTHER PUBLICATIONS

Jang to "Simple one-pot synthesis of Rh-Fe3O4 heterodimer nanocrystals and their applications to a magnetically recyclable catalyst for efficient and selective reduction of nitroarenes and alkenes", (Chem. Commun, 2011, 47, 3601-3603).*

Shaikh et al. (Sub-nanometric Rh decorated magnetic nanoparticles as reusable catalysts for nitroarene reduction in water, Catalysis Communications 119 (2019), 134-138).*

Qiao et al. (Ferric Oxide-Supported Pt Subnano Clusters for Preferential Oxidation of CO in H2-Rich Gas at Room Temperature), ACS Catal. 2014, 4, 2113-2117.*

Machine translation of CN101767018A, publication date Jul. 7, 2010.*

Lee Y, et al. ; Recyclable rhodium nanoparticles: green hydrothermal synthesis, characterization, and highly catalytic performance in reduction of nitroarenes. ; J Nanosci Nanotechnol 13 (11) ; pp. 7477-7481 ; Nov. 2013 ; Abstract Only ;1 Page.

Shaikh, et al. ; Sub-nanometric Rh decorated magnetic nanoparticles as reusable catalysts for nitroarene reduction in water ; Catalysis Communications ; Sep. 11, 2018 ; Abstract Only ; 2 Pages.

* cited by examiner

IRON OXIDE SUPPORTED RHODIUM CATALYST FOR NITROARENE REDUCTION

STATEMENT REGARDING PRIOR DISCLOSURE BY THE INVENTORS

Aspects of this technology are described in an article "Sub-nanometric Rh decorated magnetic nanoparticles as reusable catalysts for nitroarene reduction in water" published in Catalysis Communications, 2019, 119, 134-138, on Sep. 11, 2018, which is incorporated herein by reference in its entirety.

BACKGROUND OF THE INVENTION

Technical Field

The present disclosure relates to a supported catalyst having subnano sized rhodium particles disposed on iron oxide support material and methods of making the supported catalyst. The disclosure also relates to a process of producing aromatic amines by reducing aromatic nitro compounds utilizing the supported catalyst.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Catalytic hydrogenation of nitroarenes into corresponding aromatic amines is industrially important for the production of polymers [C. O. Baker, X. Huang, W. Nelson, R. B. Kaner, Chem. Soc. Rev. 46 (2017) 1510-1525], pharmaceuticals [M. Orlandi, D. Brenna, R. Harms, S. Jostand M. Benaglia, Org. Process Res. Dev. 22 (2018) 430-445], dyes [S. Banerjee, E. B. Veale, C. M. Phelan, S. A. Murphy, G. M. Tocci, L. J. Gillespie, D. O. Frimannsson, J. M. Kelly, T. Gunnlaugsson, Chem. Soc. Rev. 42 (2013) 1601-1618], and pigments [B. K. Reddy, A. Basavarajappa, M. D. Ambhore, V. G. Anand, Chem. Rev. 117 (2017) 3420-3443]. For instance, 4-aminophenol is used in the development of black and white photography, as well as during the preparation of paracetamol. However, nitrophenol is considered an environmental pollutant since it is highly toxic and inhibitory in nature [A. Corma, H. Garcia, Chem. Soc. Rev. 37 (2008) 2096-2126; and S. Francis, S. Joseph, E. P. Koshy, B. Mathew, Environ. Sci. Pollut. Res. 24 (2017) 17347-17357]. Efficient conversion of nitroarenes to aromatic amines is challenging because high catalytic activity often compromises reaction selectivity. As such, numerous catalytic processes using supported solid phases have been studied [P. Serna, A. Corma, ACS Catal. 5 (2015) 7114-7121; Q. Xiao, S. Sarina, E. R. Waclawik, J. Jia, J. Chang, J. D. Riches, H. Wu, Z. Zheng, H. Zhu, ACS Catal. 6 (2016) 1744-1753; S. M. El-Sheikh, A. A. Ismail, J. F. Al-Sharab, New J. Chem. 37 (2013) 2399-2407; Z. Dong, X. Le, C. Dong, W. Zhang, X. Li, J. Ma, Appl. Catal. B:162 (2015) 372-380; Z. Dong, X. Le, Y. Liu, C. Dong, J. Ma, J. Mat. Chem. A 2 (2014) 18775-18785; and Z. Dong, X. Le, X. Li, W. Zhang, C. Dong, J. Ma, Appl. Catal. B: 158 (2014) 129-135]. For example, Corma et al. [M. J. Climent, A. Corma, J. C. Hernandez, A. B. Hungria, S. Iborra, S. Martinez-Silvestre, J. Catal. 292 (2012) 118-129, incorporated herein by reference in its entirety] reported hydrogenation of functionalized nitroarenes into corresponding amines with excellent conversion and selectivity using $TiO_2$ or $Fe_2O_3$ supported gold nanoparticles. Recently, Rahul et al. [P. Pachfule, S. Kandambeth, D. D. D₁'az, R. Banerjee, Chem. Commun. 50 (2014) 3169-3172] reported the application of COFs (covalent organic frameworks) supported gold nanoparticles for the reduction of nitrophenol. Ellisa et al. [A. Serr'a, X. Alcob'e, J. Sort, J. Nogu'esed, E. Vall'es, J. Mater. Chem. A, 4 (2016) 15676-15687, incorporated herein by reference in its entirety] observed good catalytic activity of CoPt nanowires in the reduction of nitrophenol with sodium borohydride ($NaBH_4$). Gold nanoparticles on cyanuric acid support developed by Liu et al. [H. Guo, Y. Ren, Q. Cheng, D. Wang, Y. Liu, Catal. Commun. 102 (2017) 136-140] were tested for reducing nitrophenol. Colloidal gold-supported catalysts have been found to be efficient for the reduction of functionalized nitro compounds under certain reaction conditions [Y. Zhang, S. Liu, W. Lu, L. Wang, J. Tian, X. Sun, Catal. Sci. Technol. 1 (2011) 1142-44; and X.-B. Lou, L. He, Y. Qian, Y.-M. Liu, Y. Cao, K.-N. Fan, Adv. Synth. Catal. 353 (2011) 281-286]. Despite these efforts, the efficacy of the reported catalysts is only moderate. Furthermore, most of these studies employ sodium borohydride or hydrazine as the hydrogen source. These hazardous substances are not ideally practical because sodium borohydride is highly flammable and hydrazine is toxic and a potential carcinogen [S. M. Hussain, J. M. Frazier, Toxicol. Sci. 69 (2002) 424-432].

Although efficient, noble metal nanocatalysts are rare because they are challenging to produce as small (1 nm or less) and uniform size nanoparticles, they are not recyclable, and preparation techniques involve hazardous substances. In addition, substantial usage of additives or surfactants in the process often impedes the reusability and cost efficiency of these nanocatalysts [K. M. Koczkur, S. Mourdikoudis, L. Polavarapu, S. E. Skrabalak, Dalton Trans. 44 (2015) 17883-17905; and J. Lai, W. Niu, R. Luquea, G. Xu, Nano Today 10 (2015) 240-267, each incorporated herein by reference in their entirety].

In view of the forgoing, one objective of the present disclosure is to provide a supported catalyst having rhodium subnanoparticles disposed on a support material containing magnetic iron oxide particles. A further objective of the present disclosure is to provide a method of applying the supported catalyst as a recyclable and stable catalytic agent in chemical transformations such as reducing nitroarenes to corresponding aromatic amines.

BRIEF SUMMARY OF THE INVENTION

According to a first aspect, the present disclosure relates to a supported catalyst including a support material comprising $Fe_3O_4$, and a catalytic material comprising rhodium disposed on the support material, wherein (i) the catalytic material is in the form of subnanoparticles having an average particle size of 0.2-0.99 nm, (ii) the rhodium is present in an amount of 1-20 wt % relative to a total weight of the supported catalyst, and (iii) the support material is devoid of $Al_2O_3$.

In one embodiment, the $Fe_3O_4$ is in the form of nanospheres.

In one embodiment, the nanospheres have an average particle size of 5-25 nm.

In one embodiment, the rhodium is present in an amount of 4-10 wt % relative to a total weight of the supported catalyst.

In one embodiment, the supported catalyst has a BET surface area in a range of 100-180 m²/g.

In one embodiment, the supported catalyst has a saturation magnetization value in a range of 50-75 emu/g.

According to a second aspect, the present disclosure relates to a method of preparing the supported catalyst of the first aspect. The method involves the steps of (i) mixing the support material with a solution comprising a rhodium salt to form a suspension, (ii) heating the suspension to form a reaction mixture, and (iii) mixing a base with the reaction mixture, thereby forming the supported catalyst.

In one embodiment, the rhodium salt is rhodium(III) nitrate.

In one embodiment, the base is ammonium hydroxide.

In one embodiment, the heating is carried out at a temperature of 50-120° C.

According to a third aspect, the present disclosure relates to a process of reducing an aromatic nitro compound to an aromatic amine compound. The process involves the steps of mixing the aromatic nitro compound with a hydrogen transfer reagent in the presence of the supported catalyst of the first aspect and a solvent to form a reaction mixture, and heating the reaction mixture, thereby forming the aromatic amine compound.

In one embodiment, the hydrogen transfer reagent is tetrahydroxydiboron.

In one embodiment, the supported catalyst is present in an amount of 1-50 g/mol relative to a molar amount of the aromatic nitro compound.

In one embodiment, the reaction mixture is heated at a temperature of 30-80° C.

In one embodiment, the reaction mixture is heated for 0.5-300 minutes.

In one embodiment, the solvent is water.

In one embodiment, the aromatic nitro compound is at least one selected from the group consisting of nitrobenzene, 2-nitrotoluene, 3-nitrotoluene, 4-nitrotoluene, 3-nitroaniline, 4-nitroanisole, 1,3-dimethyl-2-nitrobenzene, 2-nitrophenol, 4-nitrophenol, and 1-chloro-4-nitrobenzene.

In one embodiment, the aromatic amine compound is at least one selected from the group consisting of aniline, 2-methylaniline, 3-methylaniline, 4-methylaniline, 1,3-diaminobenzene, 4-methoxyaniline, 2,6-dimethylaniline, 2-aminophenol, 4-aminophenol, and 4-chloroaniline.

In one embodiment, the process has an aromatic amine compound yield of 35-99.9 mole % relative to a molar amount of the aromatic nitro compound.

In one embodiment, the process further involves the steps of separating the supported catalyst from the aromatic amine compound, and reusing the supported catalyst.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 3B is a SEM image of supported catalyst 1a.

FIG. 5A is an elemental mapping of iron of supported catalyst 1a.

FIG. 5B is an elemental mapping of rhodium of supported catalyst 1a.

FIG. 7A is a scanning transmission electron microscope (STEM) image of supported catalyst 1a.

FIG. 8A is a STEM image of supported catalyst 1a.

FIG. 8B is an energy-dispersive X-ray spectrum (EDS) of supported catalyst 1a.

FIG. 13B shows $N_2$ gas adsorption isotherms of supported catalysts 1a.

DETAILED DESCRIPTION OF THE EMBODIMENTS

Figure 1A:
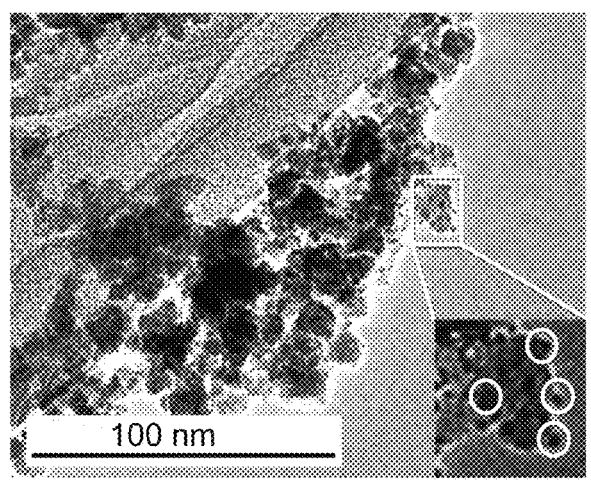
FIG. 1A is a transmission electron microscopy (TEM) image of supported catalyst 1a (4.2 wt % Rh@$Fe_3O_4$) with a magnified view inset showing rhodium subnanoparticles decorated on $Fe_3O_4$ particles.

Embodiments of the present disclosure will now be described more fully hereinafter with reference to the accompanying drawings, in which some, but not all embodiments of the disclosure are shown.

The present disclosure may be better understood with reference to the following definitions. As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out.

As used herein, the term "compound" refers to a chemical entity, whether in a solid, liquid or gaseous phase, and whether in a crude mixture or purified and isolated. The present disclosure includes all hydration states of a given compound or formula, unless otherwise noted.

According to a first aspect, the present disclosure relates to a supported catalyst including a support material comprising $Fe_3O_4$, and a catalytic material comprising rhodium disposed on the support material.

A particle is defined as a small object that behaves as a whole unit with respect to its transport and properties. An average diameter (e.g., average particle size) of the particle, as used herein, and unless otherwise specifically noted, refers to the average linear distance measured from one point on the particle through the center of the particle to a point directly across from it. For a circle, an oval, an ellipse, and a multilobe, the term "diameter" refers to the greatest possible distance measured from one point on the shape through the center of the shape to a point directly across from it. For polygonal shapes, the term "diameter", as used herein, and unless otherwise specified, refers to the greatest possible distance measured from a vertex of a polygon through the center of the face to the vertex on the opposite side.

Nanoparticles are particles between 1 and 100 nm in size. Subnanoparticles are particles with less than 1 nm diameter in size. The exceptionally high surface area to volume ratio of nanoparticles and subnanoparticles may cause them to exhibit significantly different or even novel properties from those observed in individual atoms/molecules, fine particles and/or bulk materials. In one or more embodiments, the rhodium of the present disclosure is present in the form of subnanoparticles. In a preferred embodiment, the rhodium subnanoparticles have an average particle size of 0.2-0.99 nm, 0.25-0.95 nm, 0.3-0.9 nm, 0.35-0.85 nm, 0.4-0.8 nm, 0.45-0.75 nm, 0.5-0.7 nm, 0.55-0.65 nm, or 0.6-0.62 nm. In some embodiments, the rhodium subnanoparticles are in the form of at least one shape such as a sphere, a rod, a cylinder, a rectangle, a triangle, a pentagon, a hexagon, a prism, a disk, a platelet, a flake, a cube, a cuboid, and an urchin (e.g., a globular particle possessing a spiky uneven surface).

In one embodiment, the rhodium subnanoparticles of the present disclosure are monodisperse, having a coefficient of variation or relative standard deviation, expressed as a percentage and defined as the ratio of the particle size standard deviation (σ) to the particle size mean (0 multiplied by 100 of less than 25%, preferably less than 10%, preferably less than 8%, preferably less than 6%, preferably less than 5%, preferably less than 4%, preferably less than 3%, preferably less than 2%. In a preferred embodiment, the rhodium subnanoparticles are monodisperse having a particle size distribution ranging from 80% of the average particle size to 120% of the average particle size, preferably 90-110%, preferably 95-105% of the average particle size.

Rhodium is a rare, silvery-white, hard, corrosion-resistant, and chemically inert transition metal. Rhodium can be employed in catalyzing chemical transformations such as hydrogenation. Well known rhodium catalysts include Wilkinson's catalyst (i.e. chloridotris(triphenylphosphane) rhodium(I)). Exemplary rhodium catalyzed hydrogenations include, but are not limited to, the hydrogenation of alkenes, the hydrogenation of alkynes, the hydrogenation of aromatic cyclic arenes, and the hydrogenation of nitriles. The most common oxidation state of rhodium is Rh(III) (e.g. rhodium chloride, $RhCl_3$, rhodium(III) oxide, $Rh_2O_3$). Rhodium may exist in other oxidation states such as Rh(I) (e.g. Wilkinson's catalyst). In a preferred embodiment, the rhodium subnanoparticles of the present disclosure contain predominantly elemental rhodium (Rh(0)) (i.e. greater than 75%, more preferably greater than 80%, more preferably greater than 85%, more preferably greater than 90%, more preferably greater than 95%, more preferably greater than 99% of rhodium by weight is present in elemental rhodium.

In addition to rhodium, it is envisaged that the present disclosure may be adapted to incorporate other noble, precious and/or transition metal nanoparticles and/or subnanoparticles as the catalytic material. Examples of such metals include, but are not limited to, platinum (Pt), palladium (Pd), ruthenium (Ru), nickel (Ni), copper (Cu), osmium (Os), iridium (Ir), rhenium (Re), gold (Au), silver (Ag) and mixtures or alloys thereof. A total weight of these co-catalytic metals relative to a weight of the rhodium present in the supported catalyst is preferably no more than 25%, preferably no more than 20%, preferably no more than 15%, preferably no more than 10%, preferably no more than 5%, preferably no more than 4%, preferably no more than 3%, preferably no more than 2%, preferably no more than 1%, preferably no more than 0.5%.

As used herein, a support material refers to a material, usually a solid with a surface area, to which a catalyst is affixed. Typical support materials include various kinds of carbon, alumina, and silica. In one or more embodiment, the support material of the present disclosure comprises an iron oxide. Iron oxides are chemical compounds composed of iron and oxygen. Iron oxides are widely used and typically colored yellow, orange, red, brown or black. There are sixteen known iron oxides and oxyhydroxides. The oxides include iron (II) oxide (wustite, FeO), iron (II, III) oxide (magnetite, $Fe_3O_4$), $Fe_4O_5$, $Fe_4O_3$, and iron (III) oxide including the alpha phase (hematite, $\alpha$-$Fe_2O_3$), beta phase ($\beta$-$Fe_2O_3$), gamma phase (maghemite, $\gamma$-$Fe_2O_3$) and epsilon phase ($\epsilon$-$Fe_2O_3$). The hydroxides include iron (II) hydroxide ($Fe(OH)_2$) and iron (III) hydroxide (bernalite, $Fe(OH)_3$). The oxide/hydroxides include goethite ($\alpha$-FeOOH), akaganeite ($\beta$-FeOOH), feroxyhyte ($\delta$-FeOOH), ferrihydrite ($Fe_5HO_8 \cdot 4H_2O$ approx. or $5Fe_2O_3 \cdot H_2O$, better recast as $FeOOH \cdot 4H_2O$), high pressure FeOOH, Schertmannite (ideally $Fe_8O_8(OH)_6(SO) \cdot nH_2O$ or $Fe^{3+}_{16}O_{16}(OH,SO_4)_{12\text{-}13} \cdot 10\text{-}12H_2O$) and green rust ($Fe^{III}_x Fe^{II}_y(OH)_{3x+2y-z}(A^-)_z$ where $A^-$ is $Cl^-$ or $0.5SO_4^{2-}$). In terms of the present disclosure, the support material may comprise any of the known iron oxides or oxyhydroxides above and mixtures thereof.

Iron (III) oxide or ferric oxide is the inorganic compound with formula $Fe_2O_3$. It is one of the three main oxides of iron, the other two being iron (II) oxide (FeO) which is rare, and iron (II,III) oxide ($Fe_3O_4$) which also occurs naturally as the mineral magnetite. $Fe_2O_3$ is ferromagnetic, dark red and readily attacked by acids. $Fe_2O_3$ can be obtained in various polymorphs. In the major polymorphs, $\alpha$ and $\gamma$, iron adopts an octahedral coordination geometry, each Fe center is bound to six oxygen ligands. $\alpha$-$Fe_2O_3$ has the rhombohedral corundum structure and is the most common form. It occurs naturally as the mineral hematite which is mined as the main ore of iron. $\gamma$-$Fe_2O_3$ has a cubic structure, is metastable and converted to the alpha phase at high temperatures. It is also ferromagnetic. Several other phases have been identified, including the $\beta$-phase, which is cubic body centered, metastable, and at temperatures above 500° C. converts to alpha phase, and the epsilon phase, which is rhombic, and shows properties intermediate between alpha and gamma phase. This phase is also metastable, transforming to the alpha phase between 500 and 750° C. Additionally, at high pressure an iron oxide can exist in an amorphous form. The iron oxide in the support material may be iron (III) oxide and may have an $\alpha$ polymorph, a $\beta$ polymorph, a $\gamma$ polymorph, a $\epsilon$ polymorph or mixtures thereof.

Iron (II, III) oxide or magnetite is another main oxide of iron with formula $Fe_3O_4$. It contains both $Fe^{2+}$ and $Fe^{3+}$ ions and is sometimes formulated as $FeO \cdot Fe_2O_3$. It exhibits permanent magnetism and is ferrimagnetic, although sometimes described as ferromagnetic. Its particle size and shape can be varied by the method of production. $Fe_3O_4$ has a cubic inverse spinel structure which consists of a cubic close packed array of oxide ions where all of the $Fe^{2+}$ ions occupy half of the octahedral sites and the $Fe^{3+}$ are split evenly across the remaining octahedral sites and the tetrahedral sites. Both FeO and $\gamma$-$Fe_2O_3$ have a similar cubic close packed array of oxide ions and this accounts for the interchangeability between the three compounds on oxidation and reduction as these reactions entail a relatively small change to the overall structure. $Fe_3O_4$ samples can be non-stoichiometric. In a preferred embodiment, the iron oxide present in the support material is substantially $Fe_3O_4$.

Due to its four unpaired electrons in the 3d shell, an iron atom has a strong magnetic moment. $Fe^{2+}$ ions also have four unpaired electrons in the 3d shell and $Fe^{3+}$ ions have five unpaired electrons in the 3d shell. Thus, when crystals are formed from iron atoms or $Fe^{2+}$ and $Fe^{3+}$ ions they can be ferromagnetic, antiferromagnetic or ferrimagnetic states. The ferrimagnetism of $Fe_3O_4$ arises because the electron spins of the $Fe^{II}$ and $Fe^{III}$ ions in the octahedral sites are coupled and the spins of the $Fe^{III}$ ions in the tetrahedral sites are coupled but anti-parallel to the former. The net effect is that the magnetic contributions of both sets are not balanced and there is permanent magnetism.

In the paramagnetic state, the individual atomic magnetic moments are randomly oriented, and the substance has a zero net magnetic moment if there is no magnetic field. These materials have a relative magnetic permeability greater than one and are attracted to magnetic fields. The magnetic moment drops to zero when the applied field is removed. However, in a ferromagnetic material, all the atomic moments are aligned even without an external field. A ferrimagnetic material is similar to a ferromagnet but has two different types of atoms with opposing magnetic moments. The material has a magnetic moment because the opposing moments have different strengths. If they have the same magnitude, the crystal is antiferromagnetic and possesses no net magnetic moment. Superparamagnetism is a form of magnetism, which appears in small ferrimagnetic or ferromagnetic nanoparticles. In sufficiently small nanoparticles, magnetization can randomly flip direction under the influence of temperature. In a preferred embodiment, the iron oxide present in the support material is superparamagnetic, paramagnetic, ferromagnetic, antiferromagnetic and/or ferrimagnetic, more preferably the iron oxide in the support material possesses permanent magnetism and comprises magnetite ($Fe_3O_4$) and/or its oxidized form maghemite ($\gamma$-$Fe_2O_3$), most preferably the iron oxide in the support material possess permanent magnetism and is $Fe_3O_4$ (magnetite).

In one or more embodiments, the support material of the currently disclosed supported catalyst is substantially free of aluminum oxide ($Al_2O_3$), for instance, the support material comprises less than 0.1 wt % of aluminum oxide, preferably less than 0.05 wt %, more preferably less than 0.01 wt % of aluminum oxide, relative to a total weight of the support material. In at least one embodiment, the support material is devoid of aluminum oxide.

Nanoparticles may be classified according to their dimensions. Three-dimensional nanoparticles preferably have all dimensions of less than 100 nm, and generally encompass isodimensional nanoparticles. Examples of three dimensional nanoparticles include, but are not limited to nanospheres, nanogranules and nanobeads. Two-dimensional nanoparticles have two dimensions of less than 100 nm, generally including diameter. Examples of two-dimensional nanoparticles include, but are not limited to, nanosheets, nanoplatelets, nanolaminas and nanoshells. One-dimensional nanoparticles have one dimension of less than 100 nm, generally thickness. Examples of one-dimensional nanoparticles include, but are not limited to, nanorods, nanotubes, nanofibers and nanowhiskers.

In a preferred embodiment, the $Fe_3O_4$ used herein is in the form of nanoparticles, which are spherical or substantially spherical (e.g. oval, oblong, etc.) in shape. Alternatively, it is envisaged that the $Fe_3O_4$ may have a more polygonal shape and may be generally cubic or rectangular. In a preferred embodiment, the $Fe_3O_4$ nanoparticles have a spherical morphology. Alternatively, the $Fe_3O_4$ nanoparticles of the present disclosure are envisaged to demonstrate a variety of morphologies including, but not limited to, nanosheets, nanoplatelets, nanocrystals, nanospheres, nanohexagons, nanodisks, nanocubes, nanowires, nanofibers, nanoribbons, nanorods, nanotubes, nanocylinders, nanogranules, nanowhiskers, nanoflakes, nanofoils, nanopowders, nanoboxes, nanostars, tetrapods, nanobelts, nanaourchins, nanofloweres, and mixtures thereof. In a preferred embodiment, at least 90% of a total population of the $Fe_3O_4$ nanoparticles used herein is in the form of nanospheres, preferably at least 95%, preferably at least 96%, preferably at least 97%, preferably at least 98%, preferably at least 99% of the total population of the $Fe_3O_4$ nanoparticles is in the form of nanospheres. In a preferred embodiment, the $Fe_3O_4$ nanoparticles of the present disclosure are in the form of spheres and have an average particle size of 5-100 nm, preferably 8-80 nm, preferably 10-60 nm, preferably 12-50 nm, preferably 15-40 nm, preferably 18-30 nm, preferably 20-25 nm. Most preferably, the $Fe_3O_4$ nanoparticles have an average particle size of 8-10 nm.

In a preferred embodiment, the $Fe_3O_4$ nanoparticles of the present disclosure are monodisperse, having a coefficient of variation or relative standard deviation, expressed as a percentage and defined as the ratio of the particle size standard deviation ($\sigma$) to the particle size mean (0 multiplied by 100 of less than 25%, preferably less than 10%, preferably less than 8%, preferably less than 6%, preferably less than 5%, preferably less than 4%, preferably less than 3%, preferably less than 2%. In a preferred embodiment, the $Fe_3O_4$ nanoparticles used herein are monodisperse having a particle size distribution ranging from 80% of the average particle size to 120% of the average particle size, preferably 90-110%, preferably 95-105% of the average particle size.

In one or more embodiments, the rhodium is present in an amount of 1-20 wt %, preferably 3-15 wt %, more preferably 4-10 wt % relative to a total weight of the supported catalyst. For example, the rhodium is present in an amount of about 4.2 wt %, about 6.5 wt %, or about 8.2 wt % relative to a total weight of the supported catalyst. In a most preferred embodiment, the rhodium is present in an amount of about 8.2 wt % relative to a total weight of the supported catalyst.

The Brunauer-Emmet-Teller (BET) theory (S. Brunauer, P. H. Emmett, E. Teller, *J. Am. Chem. Soc.* 1938, 60, 309-319, incorporated herein by reference) aims to explain the physical adsorption of gas molecules on a solid surface and serves as the basis for an important analysis technique for the measurement of a specific surface area of a material. Specific surface area is a property of solids which is the total surface area of a material per unit of mass, solid or bulk volume, or cross sectional area. In most embodiments, pore volume and BET surface area are measured by gas adsorption analysis, preferably $N_2$ adsorption analysis. In one or more embodiments, the supported catalyst of the present disclosure has a BET surface area in a range of 80-180 $m^2/g$, preferably 100-150 $m^2/g$, more preferably 110-140 $m^2/g$, most preferably 120-130 $m^2/g$. In certain embodiments, the BET surface area of the support material (e.g. $Fe_3O_4$ nanoparticles) may be at least 9% greater than that of the supported catalyst disclosed herein, preferably at least 10%, preferably at least 11%, preferably at least 12%, preferably at least 13%, preferably at least 14%, preferably at least 15%, preferably at least 20% greater than that of the supported catalyst (see FIGS. 13A-D). The observed smaller surface area of the supported catalyst may be due to the blocking of some pores of magnetite particles upon deposition of rhodium onto the support material.

In preferred embodiments, the catalytic material comprising rhodium is disposed on the support material. As used herein, "disposed on" describes being completely or partially filled throughout, saturated, permeated, and/or infused. The catalytic material may be affixed on one or more surfaces of the support material. For example, the catalytic material may be affixed on an outer surface of the support material and/or within pore spaces of the support material. The catalytic material may be affixed to the support material in any reasonable manner, such as physisorption, chemisorption, or combinations thereof. In one embodiment, greater than 10% of the surface area (i.e. outer surface and pore spaces) of the support material is covered by the catalytic material. Preferably greater than 15%, preferably greater than 20%, preferably greater than 25%, preferably greater than 30%, preferably greater than 35%, preferably greater than 40%, preferably greater than 45%, preferably greater than 50%, preferably greater than 55%, preferably greater than 60%, preferably greater than 65%, preferably greater than 70%, preferably greater than 75%, preferably greater than 80%, preferably greater than 85%, preferably greater than 90%, preferably greater than 95%, preferably greater than 96%, preferably greater than 97%, preferably greater than 98%, or preferably greater than 99% of the surface area of the support material is covered by the catalytic material.

In one or more embodiments, the catalytic material particles (e.g. rhodium subnanoparticles) are evenly arranged on the support material, i.e. a distance between a rhodium subnanoparticle and all its neighbors is the same or substantially the same. The distance can be said to be substantially the same when the shortest distance is at least 80%, at least 85%, at least 90%, or at least 95% of the average distance and the longest distance is not more than 120%, not more than 110%, or not more than 105% of the average distance. The distance is measured from a center of a rhodium subnanoparticle to a center of a neighboring particle. Alternatively, the catalytic material particles (e.g. rhodium subnanoparticles) are randomly arranged on the support material, i.e. distances between a rhodium subnanoparticle and its neighboring particles are different. In certain embodiments, the different catalytic materials including the rhodium species and their distributions on the support material may be identified by techniques including, but not limited to, energy dispersive X-ray spectroscopy (elemental mapping), XRD (X-ray diffraction), Raman spectroscopy, AFM (atomic force microscope), TEM (transmission electron microscopy), UV-vis spectroscopy, and EPR (electron paramagnetic resonance).

The supported catalyst disclosed herein in any of its embodiments may be in the form of nanoparticles and have an average particle size of 5-110 nm, preferably 8-90 nm, preferably 10-70 nm, preferably 12-60 nm, preferably 15-50 nm, preferably 18-40 nm, preferably 20-30 nm. The supported catalyst nanoparticles may be agglomerated or, preferably, non-agglomerated (i.e. the supported catalyst nanoparticles are well separated from one another and do not form clusters). In one embodiment, the supported catalyst nanoparticles are agglomerated and the agglomerates have an average diameter in a range of 10-400 nm, 40-200 nm, or 80-100 nm. The supported catalyst nanoparticles may be crystalline, polycrystalline, nanocrystalline, or amorphous. Preferably, the supported catalyst nanoparticles are nanocrystalline. The supported catalyst nanoparticles may have multiple phases or a single phase.

The supported catalyst disclosed herein in any of its embodiments may have a saturation magnetization value in a range of 45-80 emu/g, 50-75 emu/g, 55-70 emu/g, or 60-65 emu/g. The magnetic susceptibilities may be measured with a laboratory magnetometer such as a vibrating sample magnetometer, a superconducting quantum interference device, inductive pickup coils, a pulsed field extraction magnetometer, a torque magnetometer, a faraday force magnetometer, and an optical magnetometer. As used herein, the term "coercivity" refers to the resistance of a magnetic material to changes in magnetization, and is equivalent to the field intensity necessary to demagnetize the fully magnetized material. The supported catalyst may have a coercivity (Hc) in a range of 0.5-5 Oe, 0.8-4 Oe, 1.5-3 Oe, or 2-2.5 Oe. The presence of magnetism may provide an easy recovery of the supported catalyst of the present disclosure. For example, the supported catalyst may be insoluble in solvents and can be easily separated from other components of a reaction mixture by attracting the supported catalyst with an external magnet.

According to a second aspect, the present disclosure relates to a method of preparing the supported catalyst of the first aspect. The method involves the steps of (i) mixing the support material with a solution comprising a rhodium salt to form a suspension, (ii) heating the suspension to form a reaction mixture, and (iii) mixing a base with the reaction mixture, thereby forming the supported catalyst.

In one embodiment, $Fe_3O_4$ nanoparticles with an average particle size of 5-100 nm, preferably 8-80 nm, preferably 10-60 nm, preferably 12-50 nm, preferably 15-40 nm, preferably 18-30 nm, preferably 20-25 nm are used herein as the support material. The $Fe_3O_4$ nanoparticles may be prepared by co-precipitation methods, micro-emulsion techniques, and/or high temperature decomposition of organic precursor techniques. Alternatively, the $Fe_3O_4$ nanoparticles may be available from commercial vendors including, without limitation, Sigma Aldrich, Alfa Aesar, and US Research Nanomaterials, Inc.

Exemplary rhodium salts include, but are not limited to, rhodium(III) nitrate, rhodium(III) chloride, rhodium(III) acetylacetonate, rhodium(III) sulfate, ammonium hexachlororhodate (III), rhodium(III) oxide and hydrates and/or mixtures thereof. In a preferred embodiment, rhodium(III) nitrate is used herein as the rhodium salt. In another embodiment, it is envisaged that the present disclosure may be adapted to incorporate other sources of rhodium including, but not limited to chloro(1,5-cyclooctadiene) rhodium(I) dimer, bicycle [2.2.1]hepta-2,5-diene rhodium(I) chloride dimer, (acetylacetonato) (norbornadiene) rhodium(I), hydroxyl(cyclooctadiene) rhodium(I) dimer, chlorobis(cyclooctene) rhodium(I) dimer, 2,5-norbornadiene-rhodium(I) chloride dimer, methoxy (cyclooctadiene) rhodium(I) dimer, hydroxy [—(S)-BINAP] rhodium(I) dimer and hydrates and/or mixtures thereof.

In a preferred embodiment, the solvent used in the solution of the present method is an anhydrous polar protic solvent including, but not limited to, methanol, ethanol, n-propanol, isoproponal, and n-butanol. Most preferably, anhydrous methanol is used herein as the solvent.

The mixing may occur via stirring, shaking, sonicating, blending, or by otherwise agitating the mixture. Preferably the suspension is stirred for 0.1-8 hours, preferably 0.25-4 hours, preferably 0.5-2 hours. In one embodiment, the support material (e.g. the $Fe_3O_4$ nanoparticles) may be dispersed or mixed in a portion of the solvent by sonication for 1-6 hours, preferably 2-4 hours, or about 3 hours first, and then other components (e.g. the solution of rhodium salt) may be added and mixed via stirring to form the suspension. In one or more embodiments, a molar ratio of the rhodium salt to the support material is 1:3 to 3:1, preferably 1:2 to 2:1, more preferably 1:1.5 to 1.5:1, or about 1:1. However, in certain embodiments, the molar ratio of the rhodium salt to the support material is less than 1:3 or greater than 3:1. In one embodiment, the rhodium salt is present in the suspension at a concentration of 1-100 mM, preferably 5-75 mM, preferably 10-50 mM, preferably 20-40 mM, or about 30 mM.

The suspension may be heated at a temperature of 50-120° C., preferably 60-110° C., more preferably 70-100° C., most preferably 80-90° C. for 0.5-6 hours, 1-4 hours, or 2-3 hours to form a reaction mixture. The heating of the suspension may be conducted in inert gas (e.g. nitrogen, argon, helium). Also, in some embodiments, the heating may not be conducted in inert gas, but in a vacuum.

The supported catalyst may be formed by a reduction process under alkaline conditions. The reduction may occur at a pH in the range of 9-14, preferably 9.5-13.5, preferably 10-13, preferably 11-12.75, preferably 11.5-12.5. In a preferred embodiment, the pH is tuned and maintained by ammonium hydroxide (i.e. aqueous ammonia) but a variety of bases are envisaged, including hydroxide, carbonates, and bicarbonates of alkali metals or alkaline earth metals. The supported catalyst may precipitate and be collected with an external magnet and washed with a solvent such as water and dichloromethane to remove unreacted starting materials.

According to a third aspect, the present disclosure relates to a process of reducing an aromatic nitro compound to an aromatic amine compound. The process involves the steps of mixing the aromatic nitro compound with a hydrogen transfer reagent in the presence of the supported catalyst of the first aspect and a solvent to form a reaction mixture, and heating the reaction mixture, thereby forming the aromatic amine compound.

As used herein, the term "aromatic nitro compound" or "nitroarene" refers to an organic compound having one or more nitro groups ($—NO_2$) on an aromatic structure. The term "aromatic amine compound" refers to an organic compound having one or more amino ($—NH_2$) groups on an aromatic structure. The aromatic structure can be monocyclic or polycyclic. Examples of aromatic structures applicable to the process of the present disclosure include, but are not limited to, benzene, naphthalene, anthracene, phenanthrene, pyrene, and biphenyl. Non-limiting examples of aromatic nitro compounds include nitrobenzene, 2-nitrotoluene, 3-nitrotoluene, 4-nitrotoluene, 3-nitroaniline, 4-nitroanisole, 1,3-dimethyl-2-nitrobenzene, 5-methoxy-2-nitroaniline, 2-nitrophenol, 4-nitrophenol, 4-hydroxy-3-nitrobenzyl alcohol, 1,2-dimethyl-3-nitrobenzene, 1,2-dimethyl-4-nitrobenzene, 1,3-dimethyl-5-nitrobenzene, 1-ethyl-2-nitrobenzene, 2-methyl-3-nitroanisole, 2-methyl-4-nitroanisole, 1-nitro-2-propylbenzene, 2-nitro-p-cymene, 4-tert-butyl-2,6-dinitroanisole, 1-nitronaphthalene, 1,3-, 1,5-, 1,8-, and 2,7-dinitronaphthalene, 2-methyl-1-nitronaphthalene, 1-methoxy-4-nitronaphthalene, 2,2'-dinitrobipheny, 9-nitroanthracene, 1,3-, and 1,6-dinitropyrene. Importantly, the process disclosed herein also tolerates halonitro aromatic compounds including, but not limited to, 1-chloro-4-nitrobenzene, 1-chloro-2-nitrobenzene, 1-chloro-3-nitrobenzene, 1-bromo-4-nitrobenzene, 1-bromo-2-nitrobenzene, 1-bromo-3-nitrobenzene, 1-fluoro-4-nitrobenzene, 1-fluoro-2-nitrobenzene, 1-fluoro-3-nitrobenzene, 2-chloro-4-nitrotoluene, 2-bromo-4-nitrotoluene, 4-chloro-2-nitrotoluene, 4-bromo-2-nitrotoluene, 6-chloro-2-nitrotoluene, 3-chloro-4-nitroethylbenzene, 2,5-, 2,3-, 2,4-, 3,4-, and 3,5-dichloronitrobenzene, 3,4- and 2,4-dibromonitrobenzene, 4-chloro-6-nitrometaxylene, 3-chloro-4-nitropropylbenzene, 3-chloro-4-nitrobutylbenzene, 1-chloro-8-nitronaphthalene, 1-chloro-2-nitronaphthalene, 1-nitro-5,8-dichloronaphthalene, 3-chloro-4-fluoronitrobenzene, 2-fluoro-4-chloronitrobenzene, 2,4-difluoronitrobenzene, 2,4,5-, 2,3,5-, and 2,4,6-trichloronitrobenzene.

In one or more embodiments, the aromatic nitro compound is at least one selected from the group consisting of nitrobenzene, 2-nitrotoluene, 3-nitrotoluene, 4-nitrotoluene, 3-nitroaniline, 4-nitroanisole, 1,3-dimethyl-2-nitrobenzene, 2-nitrophenol, 4-nitrophenol, and 1-chloro-4-nitrobenzene. In related embodiments, the corresponding aromatic amine compound formed by the currently disclosed process is at least one selected from the group consisting of aniline, 2-methylaniline, 3-methylaniline, 4-methylaniline, 1,3-diaminobenzene, 4-methoxyaniline, 2,6-dimethylaniline, 2-aminophenol, 4-aminophenol, and 4-chloroaniline.

Exemplary hydrogen transfer reagents include, but are not limited to, tetrahydroxydiboron ($B_2(OH)_4$), sodium hydride (NaH), sodium borohydride ($NaBH_4$), diborane ($B_2H_6$), boric acid ($H_3BO_3$), potassium hydride (KH), calcium hydride ($CaH_2$), hydrazine ($N_2H_4$), lithium borohydride ($LiBH_4$), lithium aluminum hydride ($LiAlH_4$), and mixtures thereof. Alternatively, reducing agents such as hydrogen gas and diisobutylaluminum hydride (DIBAL) may be used. In a preferred embodiment, the hydrogen transfer reagent used herein is tetrahydroxydiboron.

The reduction performance of the supported catalyst can be controlled by adjusting conditions such as temperature, solvent and/or catalyst loading. The solvent of the presently disclosed process is preferably water, more preferably deionized water. Tetrahydroxydiboron may react with water and release hydrogen gas. Other solvents that may be used in addition to or in lieu of water include, but are not limited to, methanol, ethanol, n-propanol, isoproponal, n-butanol, DMF, DMSO, and DMA. In one or more embodiments, the supported catalyst is present in an amount of 1-50 g/mol, preferably 5-25 g/mol, more preferably 8-15 g/mol, or about 10 g/mol relative to a molar amount of the aromatic nitro compound. A higher catalyst loading (e.g. greater than 50 g/mol) may be used and the process will still proceed as intended. The heating may be carried out at a temperature in the range of 30–85° C., preferably 40-80° C., preferably 50-70° C., or about 60° C. for 0.5-600 minutes, 1-300 minutes, 5-120 minutes, 10-60 minutes, or 15-30 minutes under an inert atmosphere.

Prior to mixing with the hydrogen transfer reagent, the aromatic nitro compound and the supported catalyst may be mixed with the solvent under an inert atmosphere (e.g. nitrogen, argon, helium atmosphere) in a reaction vessel and the mixture is optionally agitated. The hydrogen transfer reagent may be added to the mixture to form a reaction mixture. In one embodiment, the aromatic nitro compound is present in the reaction mixture in an amount of 10-1,000 mM, 50-750 mM, 100-500 mM, 200-300 mM, or about 250 mM. A concentration of the hydrogen transfer reagent in the reaction mixture may be in a range of 0.1-5 M, 0.5-4 M, 1-3 M, or about 2 M. A molar ratio of the hydrogen transfer reagent to the aromatic nitro compound may be in a range of 2:1 to 20:1, 4:1 to 15:1, 6:1 to 10:1, or about 8:1.

The reaction mixture may be optionally agitated throughout the duration of the reaction by employing a rotary shaker, a magnetic stirrer, a centrifugal mixer, or an overhead stirrer. In another embodiment, the reaction mixture is left to stand (i.e. not stirred). In one embodiment, the reaction mixture is sonicated in an ultrasonic bath or with an ultrasonic probe. An external heat source, such as a water bath or an oil bath, an oven, microwave, or a heating mantle, may be employed to heat the reaction mixture. In some embodiments, the reaction mixture is heated with microwave irradiation. The progress of each reaction may be monitored by methods generally known to those of ordinary skill in the art, such as thin layer chromatography, gas chromatography, nuclear magnetic resonance, infrared spectroscopy, and high pressure liquid chromatography combined with ultraviolet detection or mass spectroscopy. Preferably, gas chromatography combined with mass spectroscopy is used. Alternatively, UV-vis absorption spectroscopy is used to monitor the progress of the reaction.

The aromatic amine compound may be isolated and purified by methods known to those of ordinary skill in the art, such as filtration through a celite containing cartridge, aqueous work-up, extraction with organic solvents, distillation, crystallization, column chromatography, and high pressure liquid chromatography (HPLC) on normal phase or reversed phase. Preferred methods include, evaporating the reaction mixture to dryness, purifying the residue with column chromatography, and recrystallization. In one or more embodiments, the process has an aromatic amine compound yield of 35-99.9 mole %, preferably 40-99 mol %, preferably 45-95 mol %, preferably 50-90 mol %, preferably 55-85 mol %, preferably 60-80 mol %, preferably 65-75 mol %, or about 70 mol % relative to a molar amount of the aromatic nitro compound.

Figure 15A:
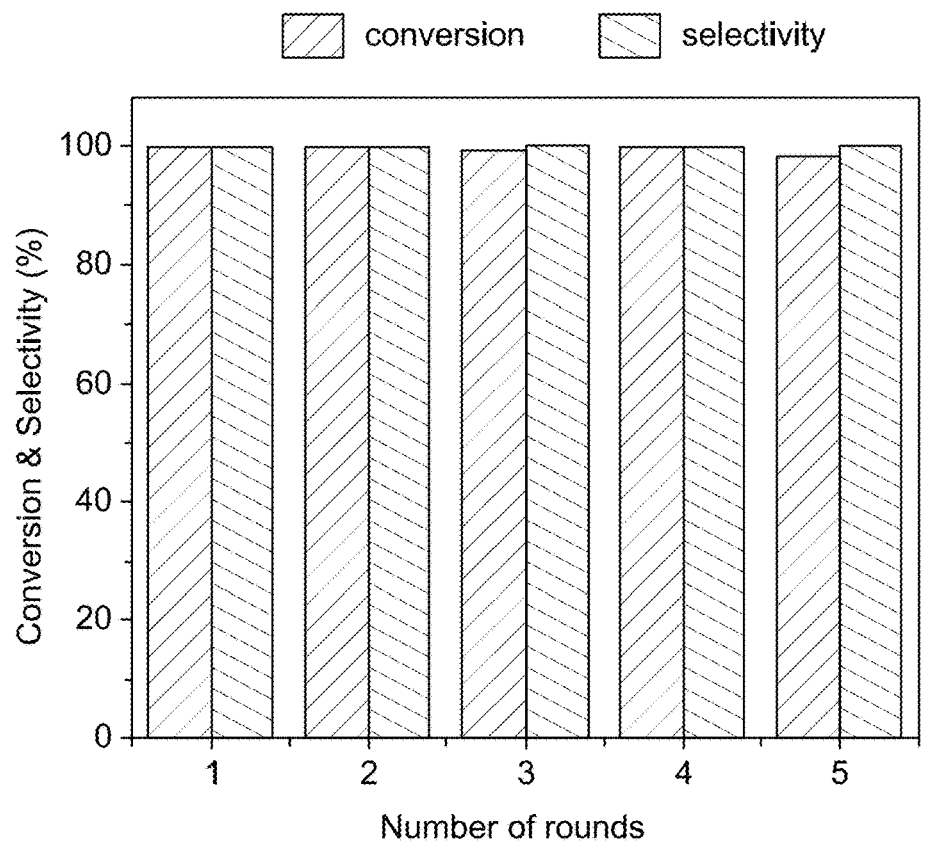
FIG. 15A is a bar graph showing reusability of supported catalyst 1c.
Figure 15B:
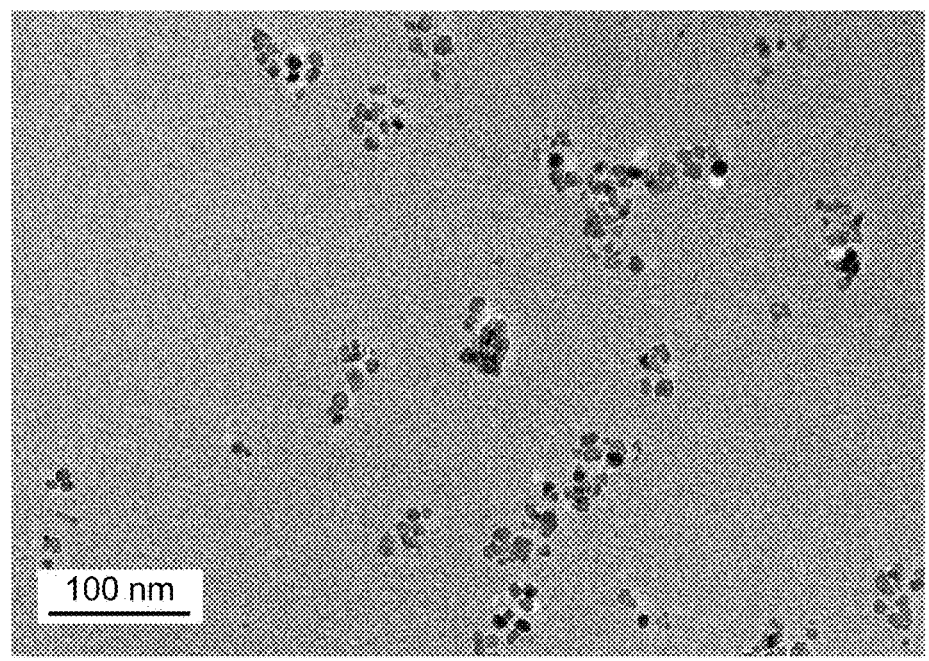
FIG. 15B is a TEM image of a supported catalyst 1c recycled after 5 rounds of catalyzing nitrobenzene reduction.
Figure 16A:
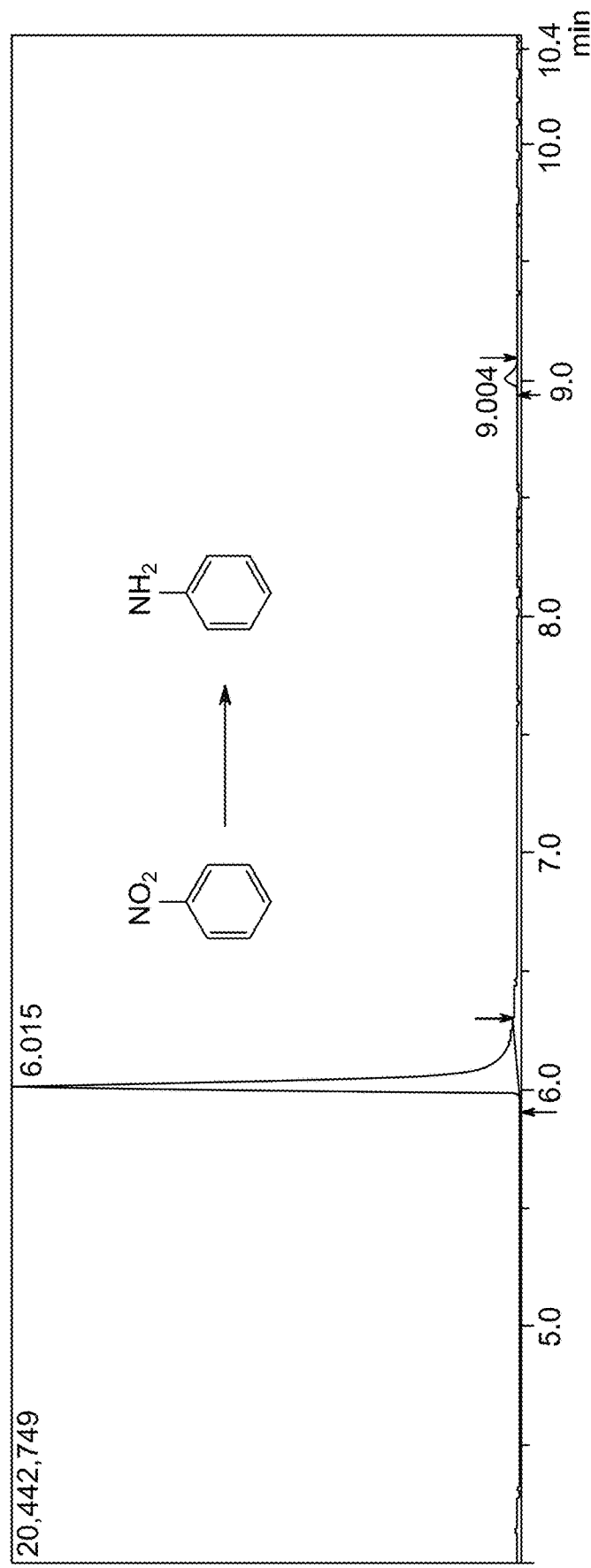
FIG. 16A is a gas chromatogram showing reaction conversion of reducing nitrobenzene by THDB in the presence of a supported catalyst.
Figure 16B:
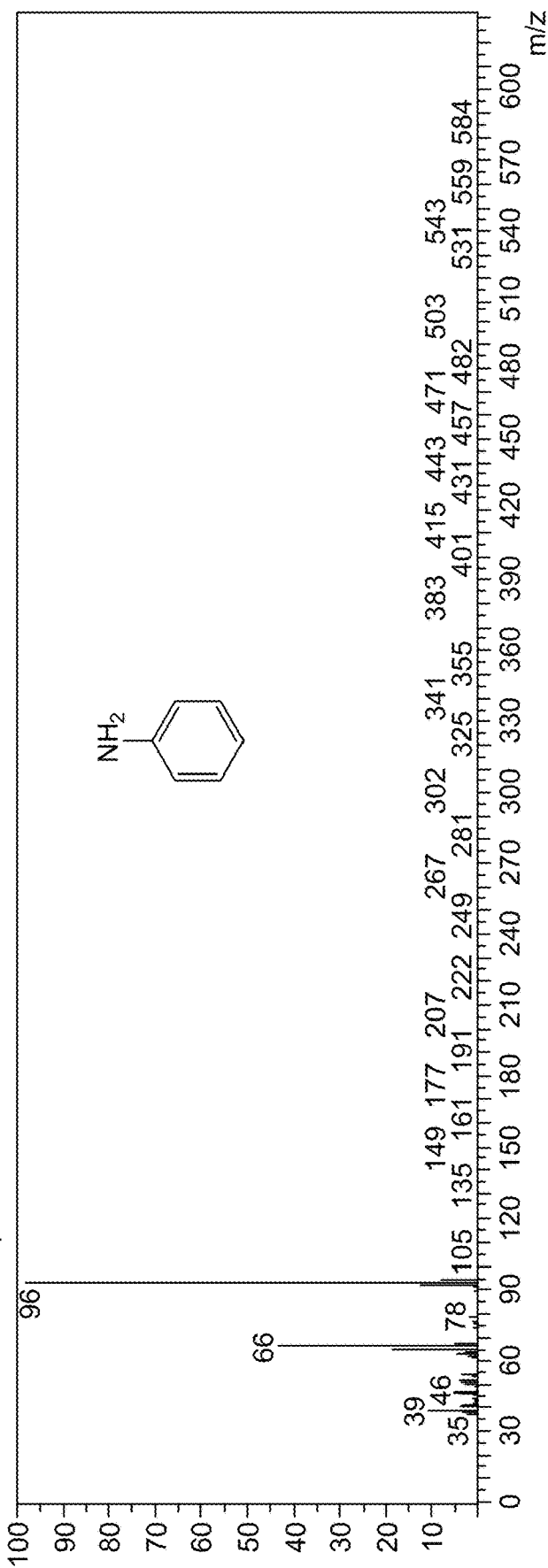
FIG. 16B is a mass spectrum identifying aniline formed by reducing nitrobenzene.
Figure 16C:
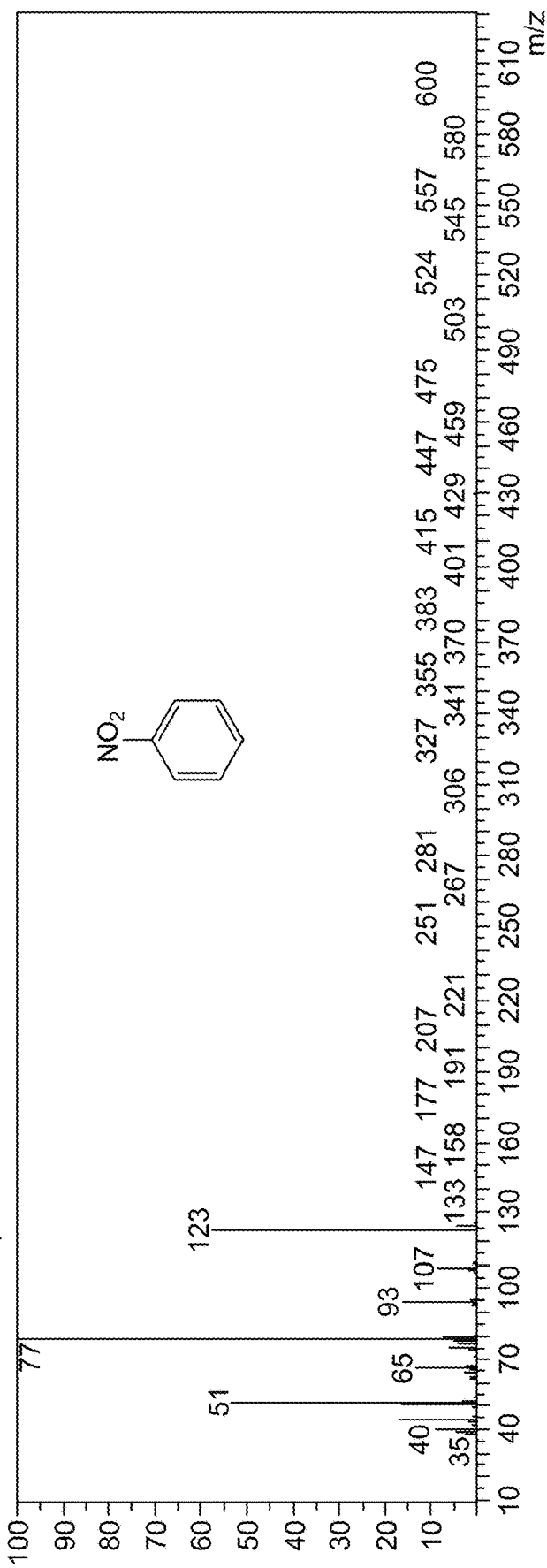
FIG. 16C is a mass spectrum identifying nitrobenzene.
Figure 17A:
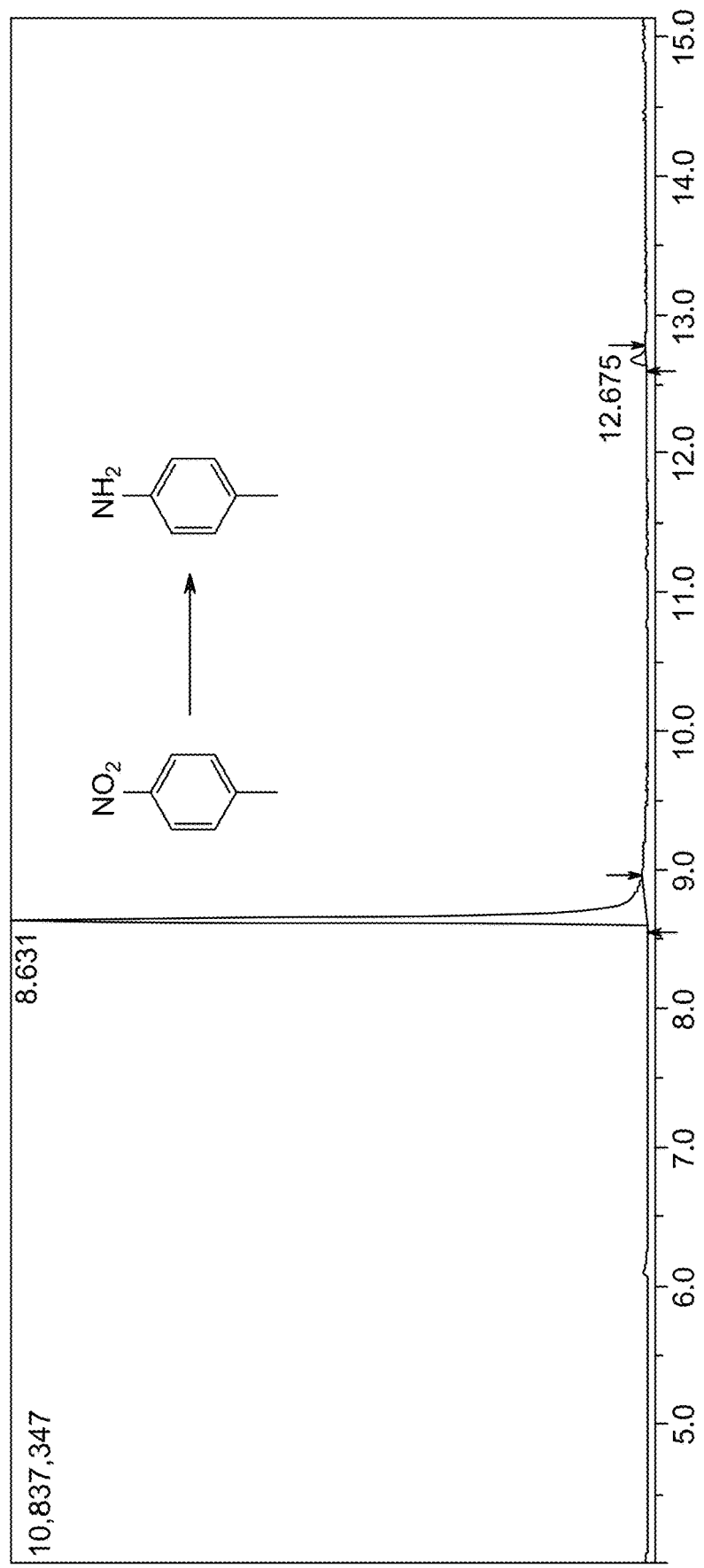
FIG. 17A is a gas chromatogram showing reaction conversion of reducing 4-nitrotoluene by THDB in the presence of a supported catalyst.
Figure 17B:
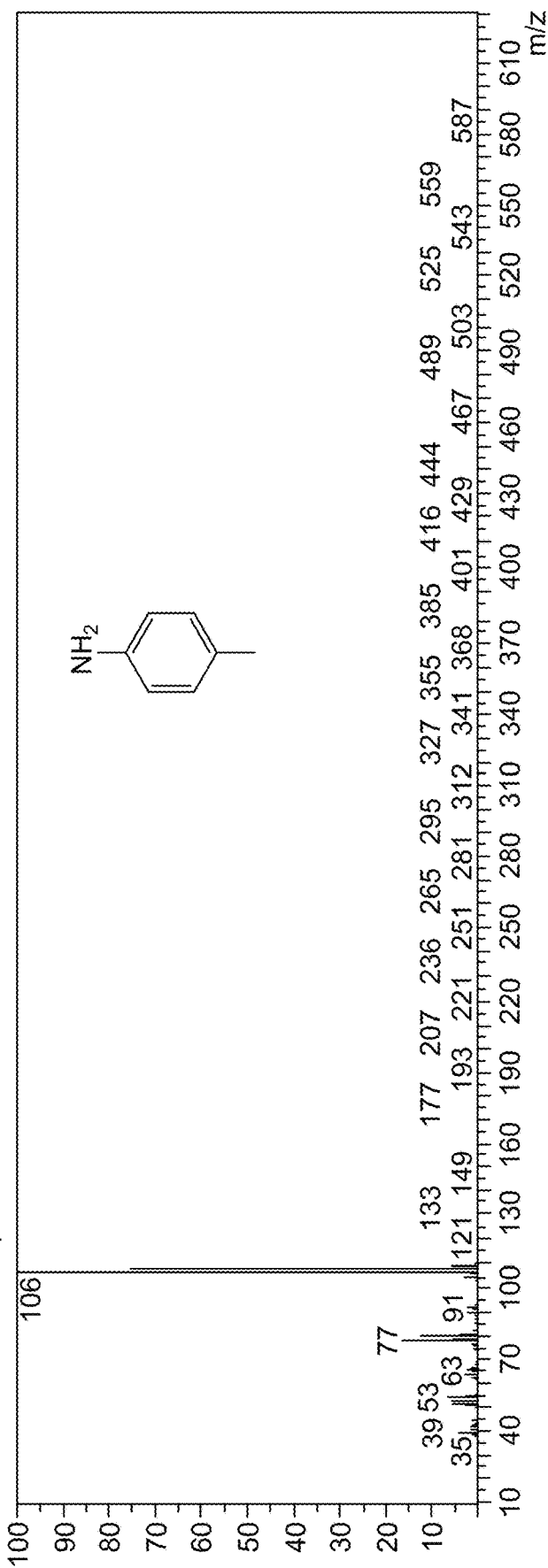
FIG. 17B is a mass spectrum identifying 4-methylaniline formed by reducing 4-nitrotoluene.
Figure 17C:
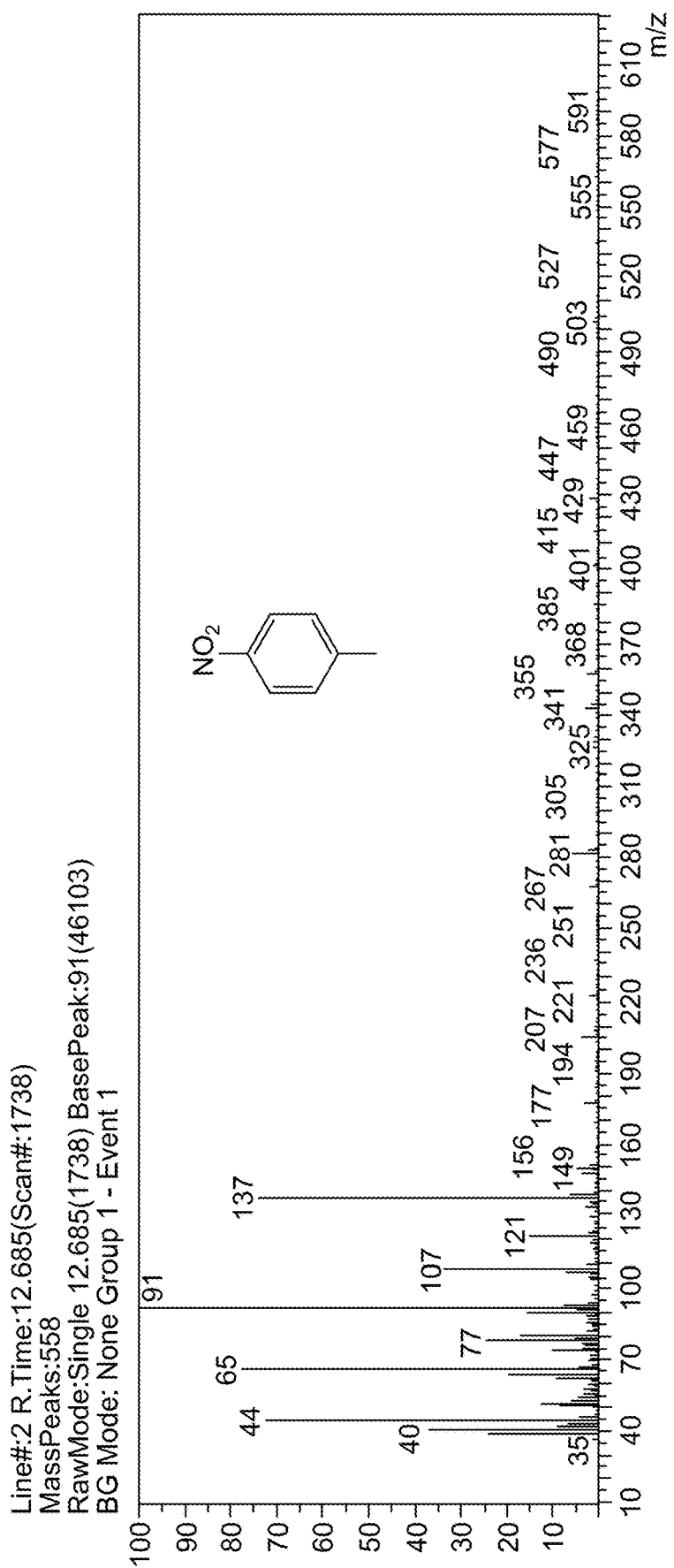
FIG. 17C is a mass spectrum identifying 4-nitrotoluene.
Figure 18A:
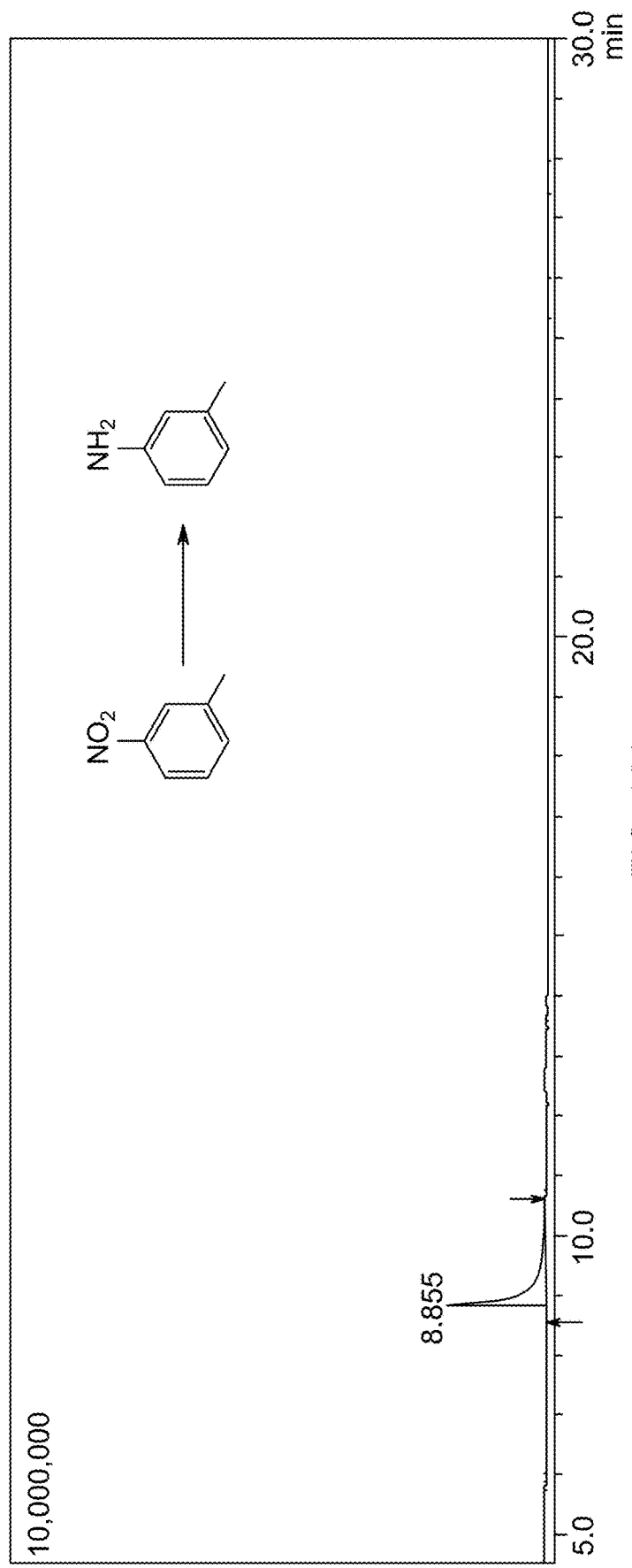
FIG. 18A is a gas chromatogram showing reaction conversion of reducing 3-nitrotoluene by THDB in the presence of a supported catalyst.
Figure 18B:
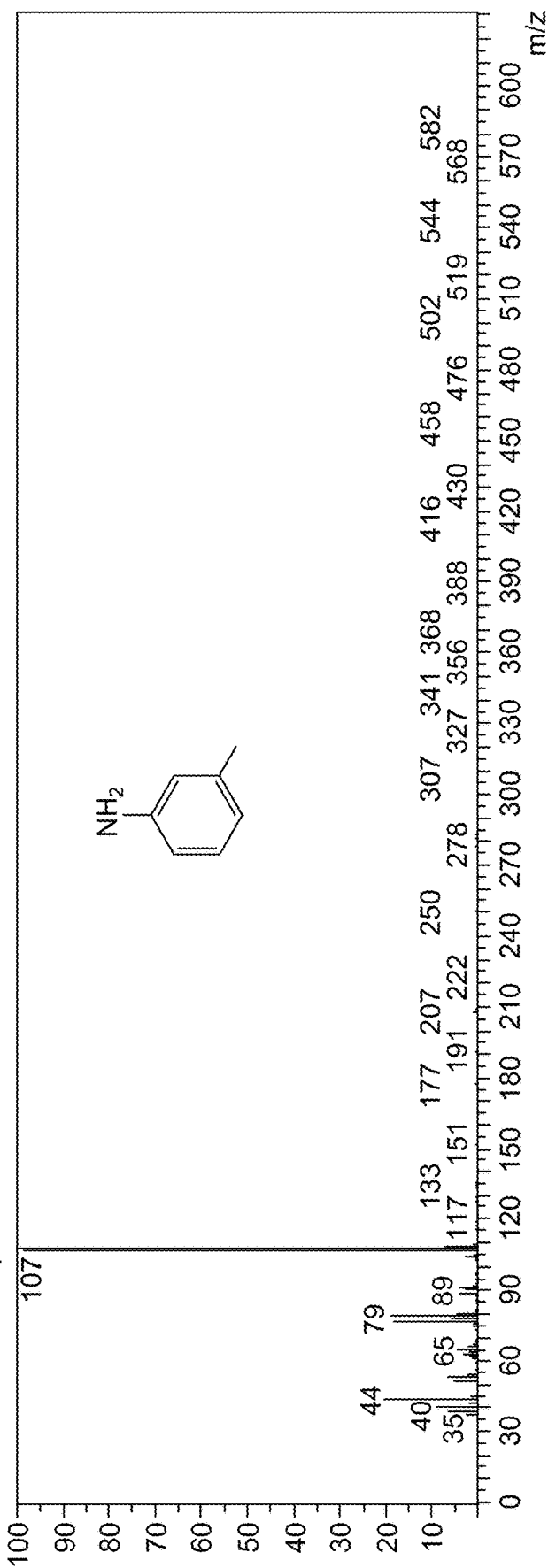
FIG. 18B is a mass spectrum identifying 3-methylaniline formed by reducing 3-nitrotoluene.
Figure 19A:
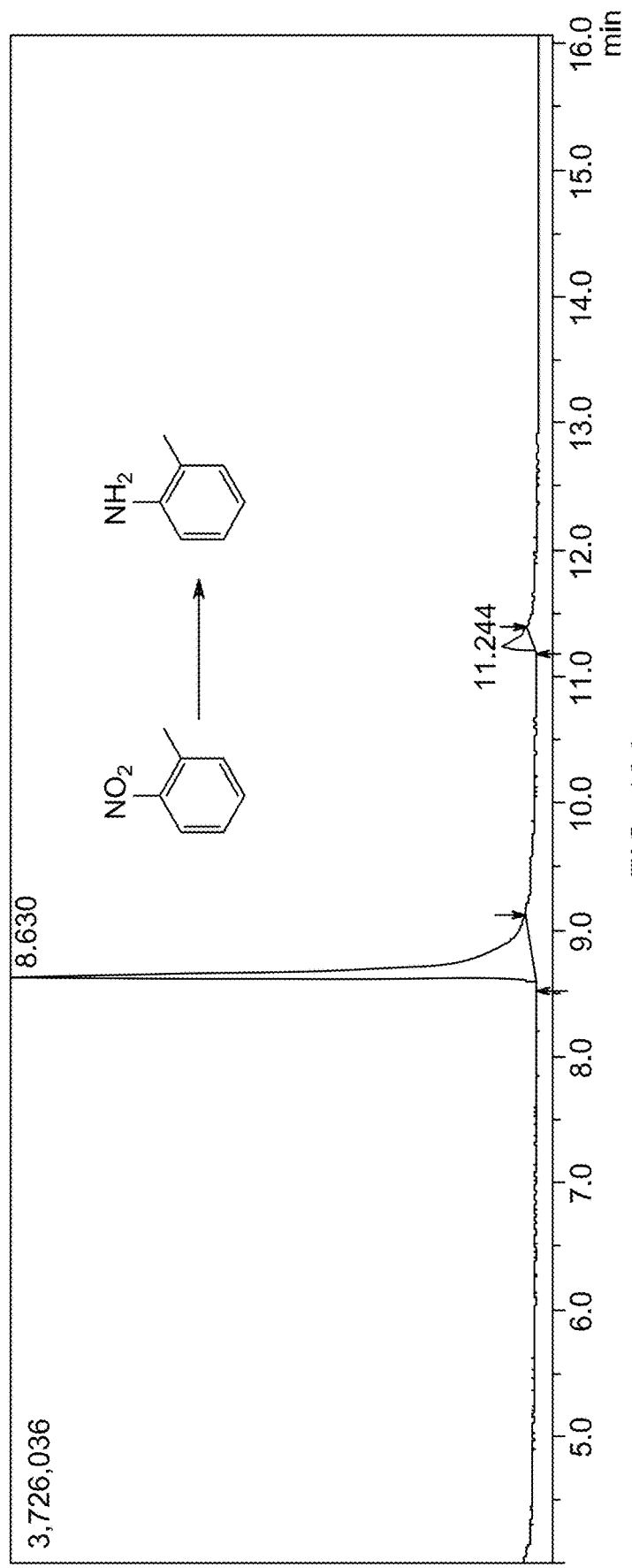
FIG. 19A is a gas chromatogram showing reaction conversion of reducing 2-nitrotoluene by THDB in the presence of a supported catalyst.
Figure 19B:
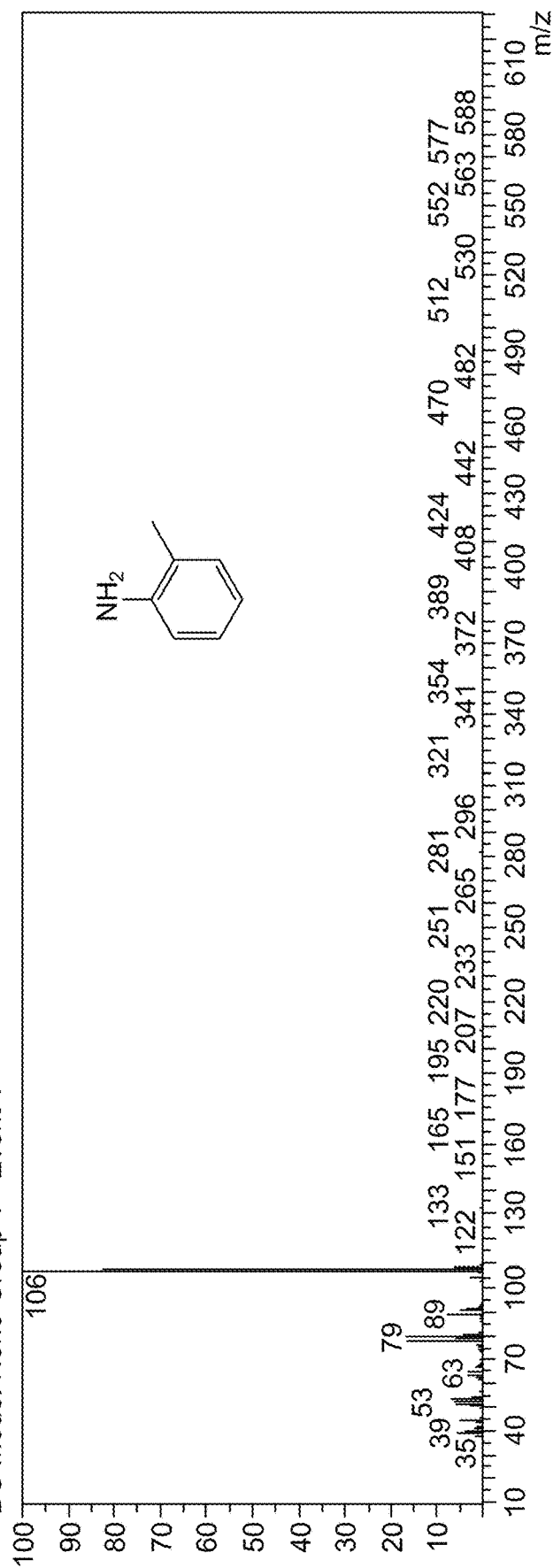
FIG. 19B is a mass spectrum identifying 2-methylaniline formed by reducing 2-nitrotoluene.
Figure 19C:
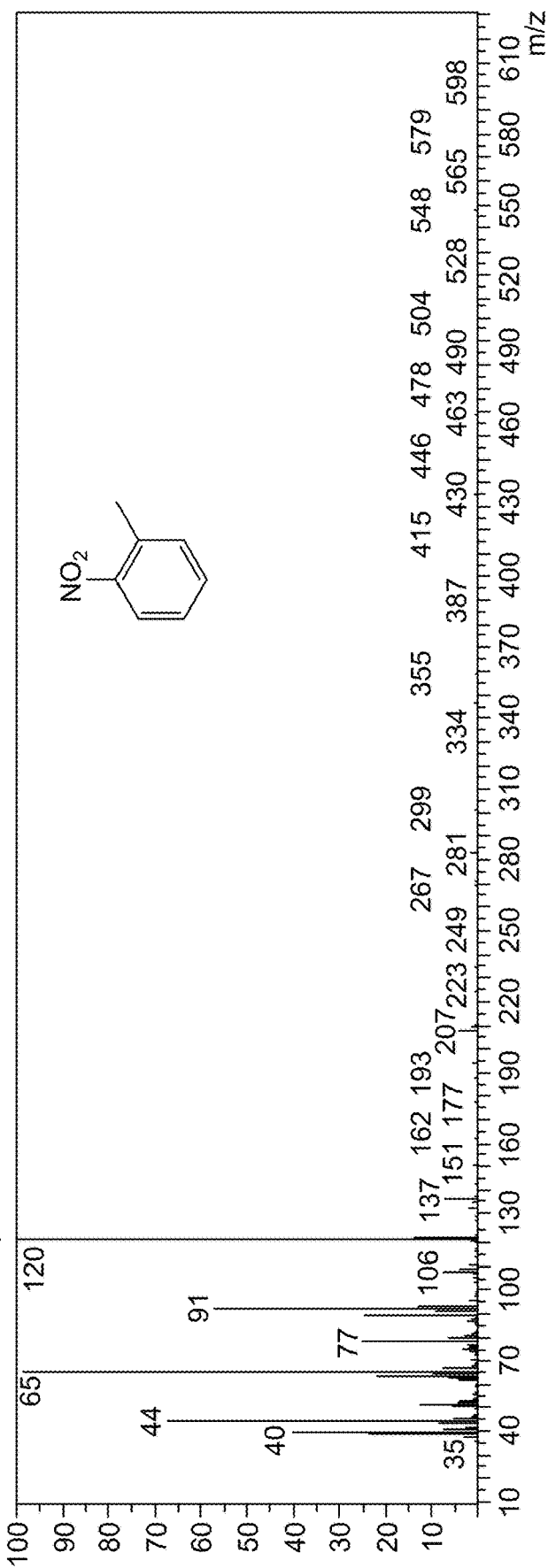
FIG. 19C is a mass spectrum identifying 2-nitrotoluene.
Figure 20A:
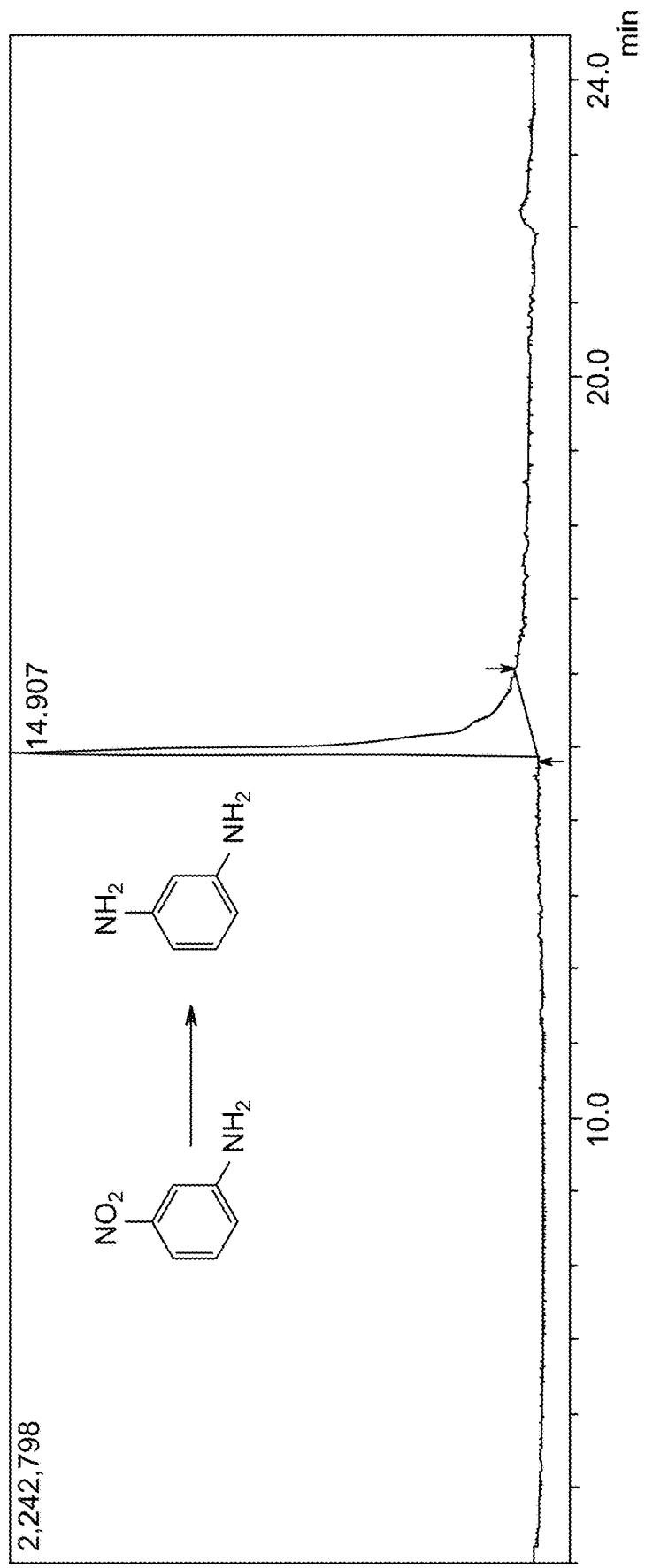
FIG. 20A is a gas chromatogram showing reaction conversion of reducing 3-nitroaniline by THDB in the presence of a supported catalyst.
Figure 20B:
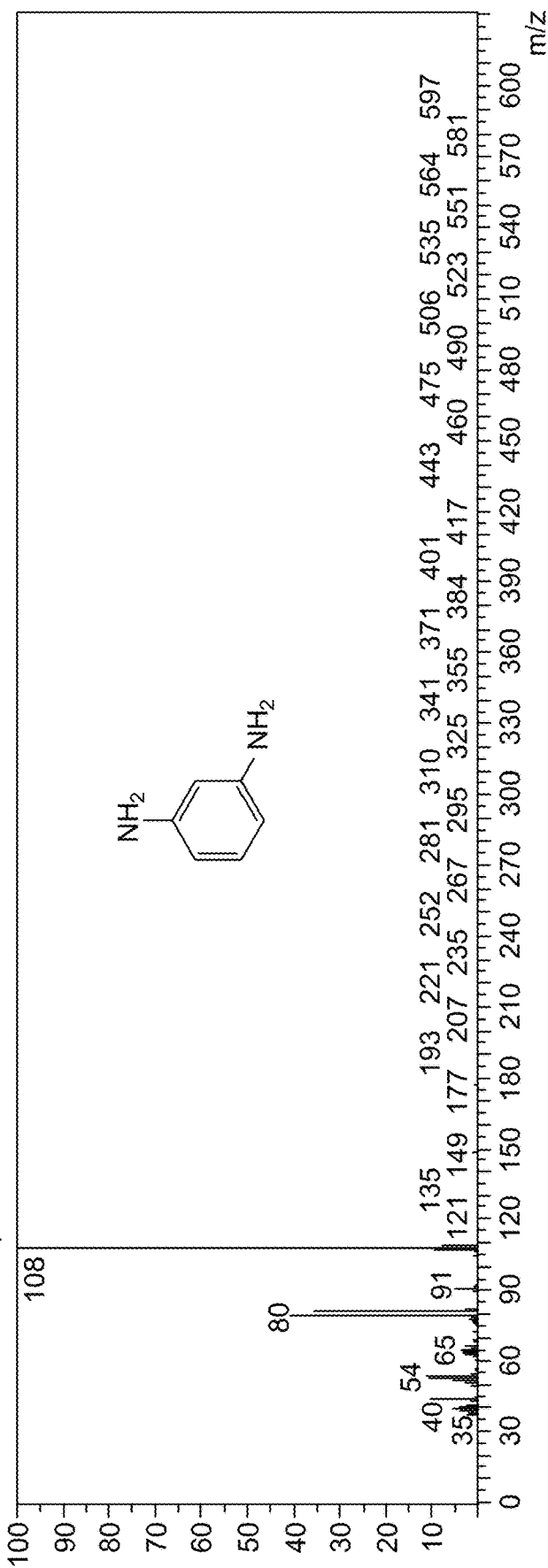
FIG. 20B is a mass spectrum identifying 1,3-diaminobenzene formed by reducing 3-nitroaniline.
Figure 21A:
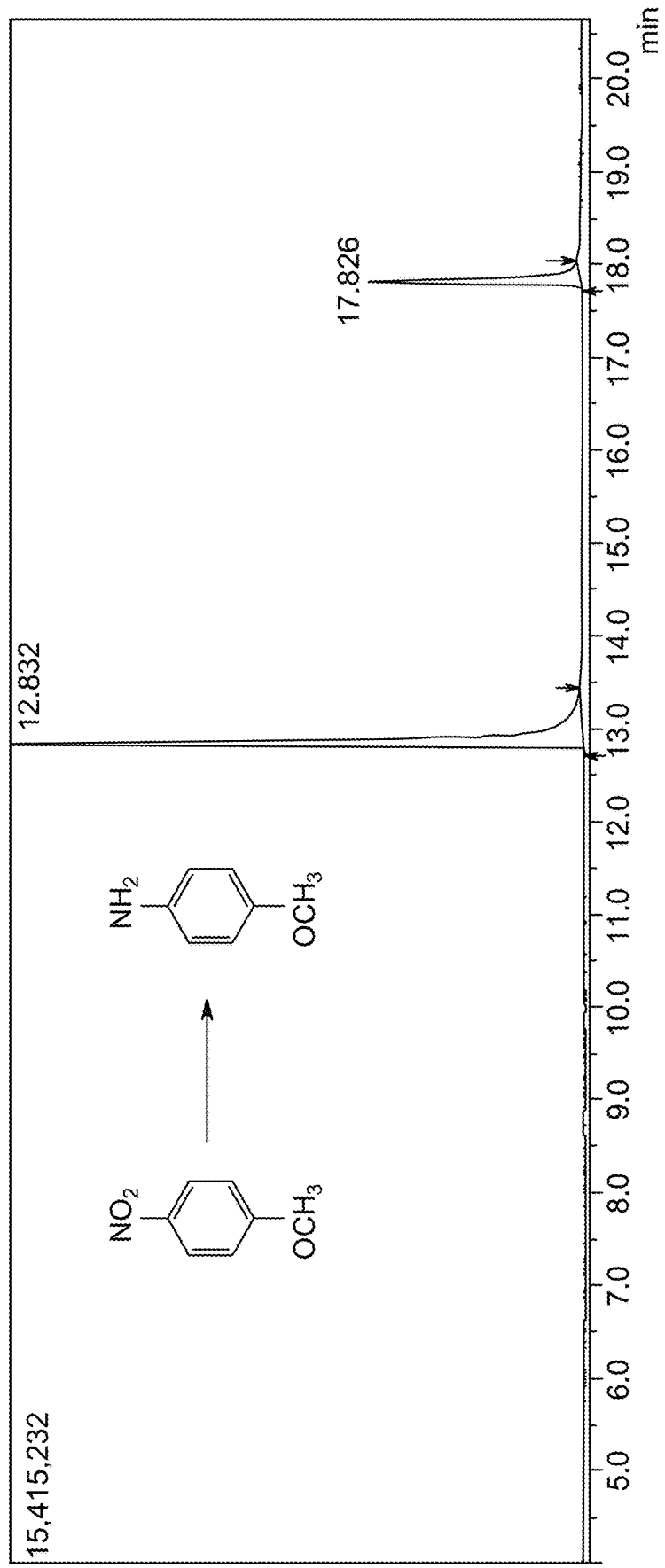
FIG. 21A is a gas chromatogram showing reaction conversion of reducing 4-nitroanisole by THDB in the presence of a supported catalyst.
Figure 21B:
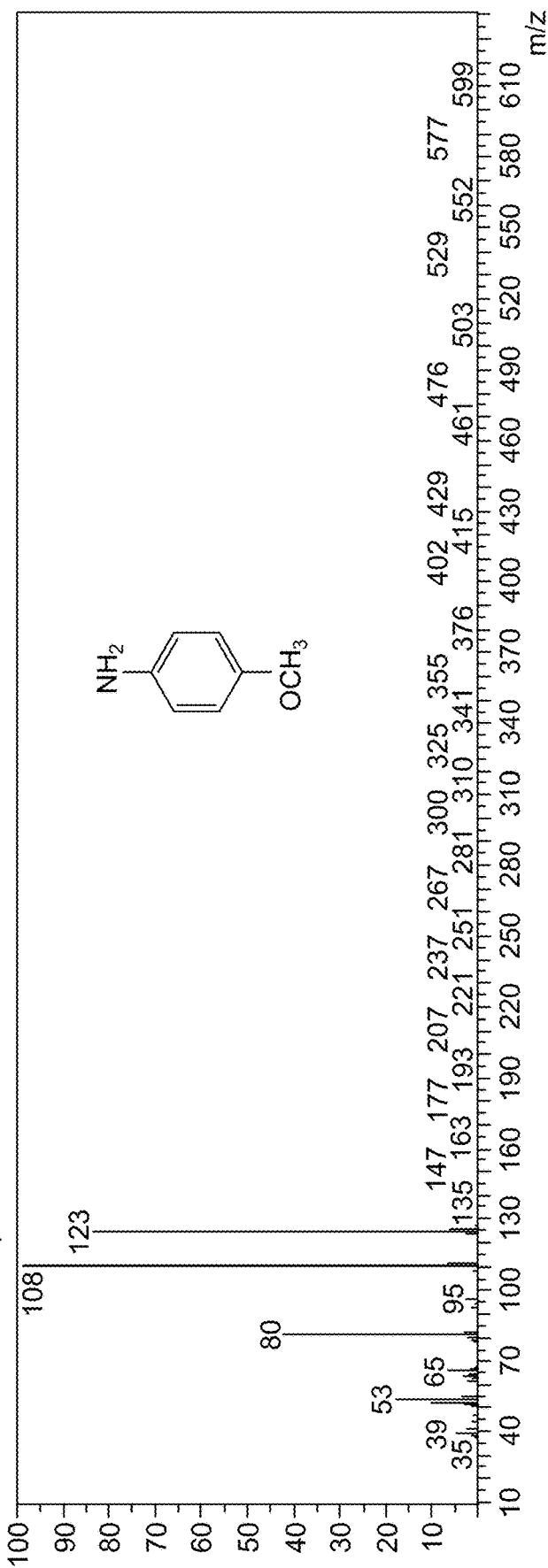
FIG. 21B is a mass spectrum identifying 4-methoxyaniline formed by reducing 4-nitroanisole.
Figure 21C:
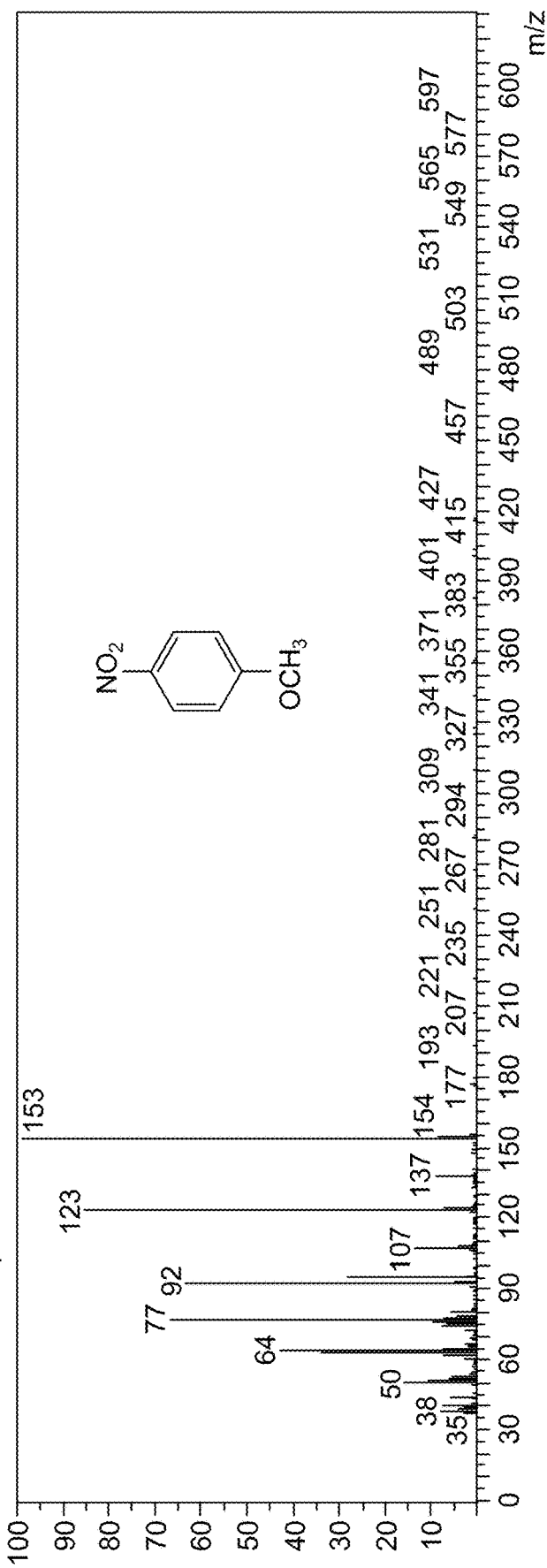
FIG. 21C is a mass spectrum identifying 4-nitroanisole.
Figure 22A:
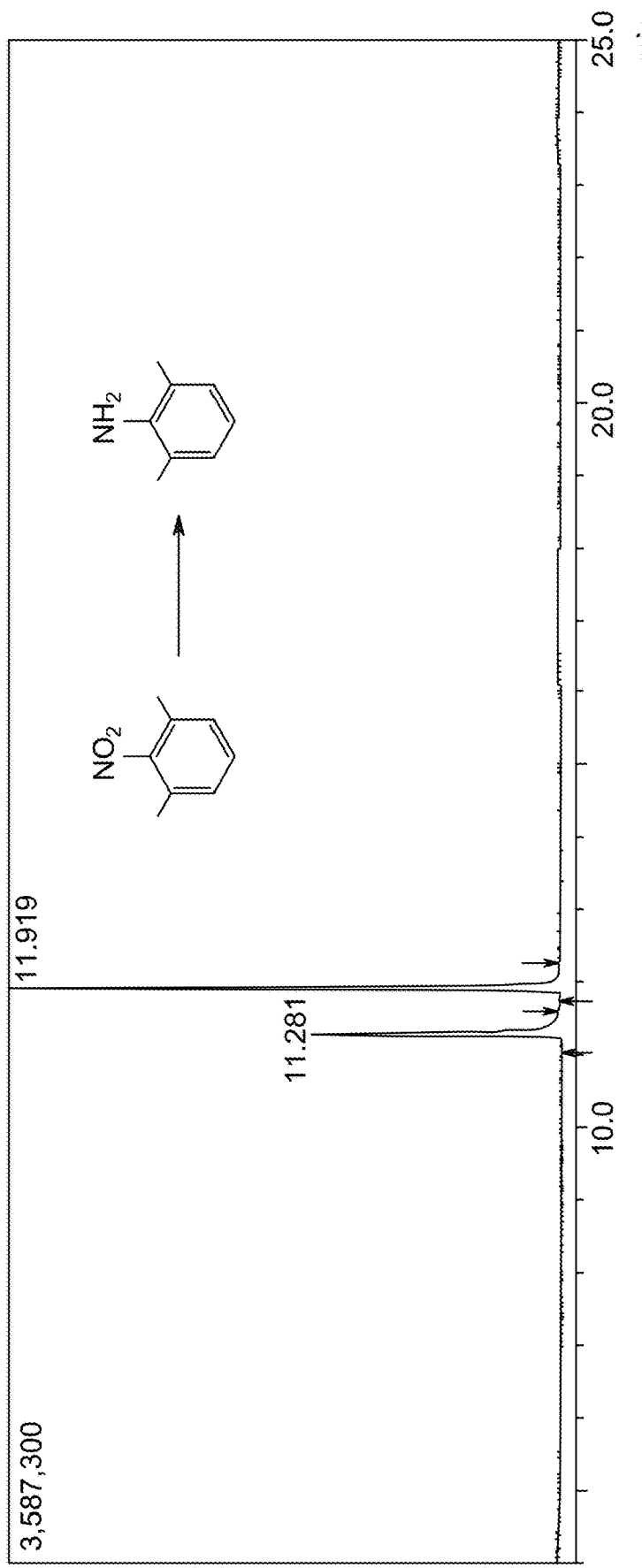
FIG. 22A is a gas chromatogram showing reaction conversion of reducing 1,3-dimethyl-2-nitrobenzene by THDB in the presence of a supported catalyst.
Figure 22B:
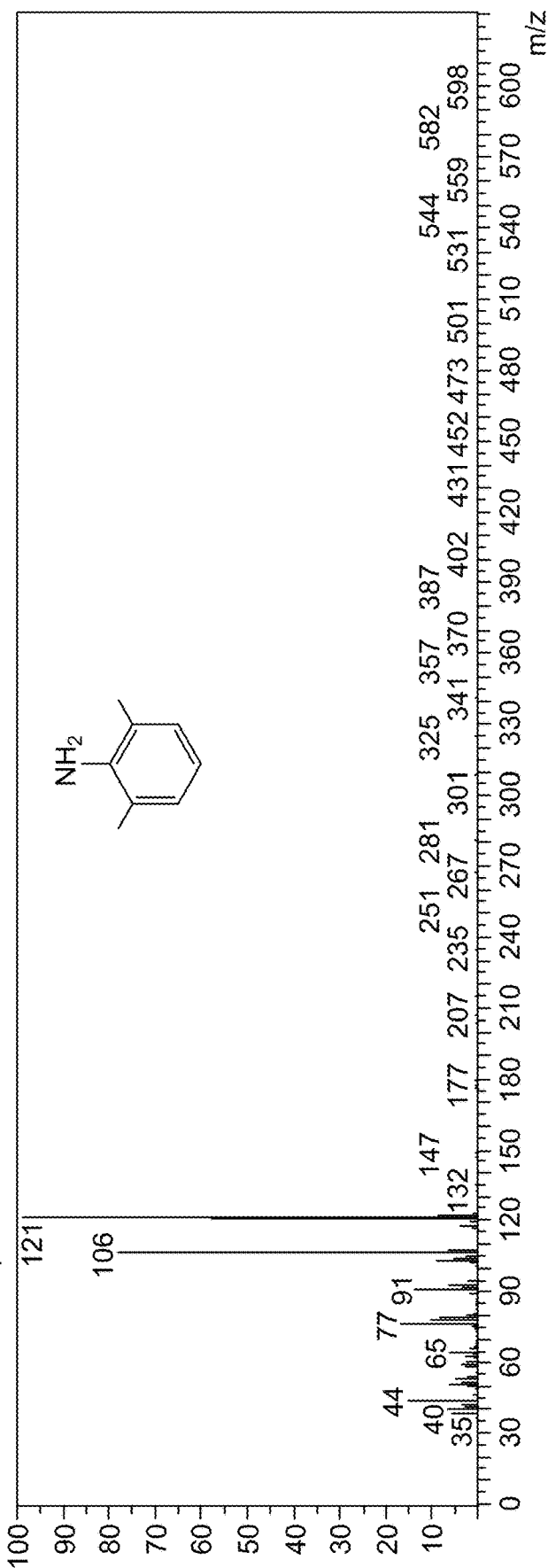
FIG. 22B is a mass spectrum identifying 2,6-dimethylaniline formed by reducing 1,3-dimethyl-2-nitrobenzene.
Figure 22C:
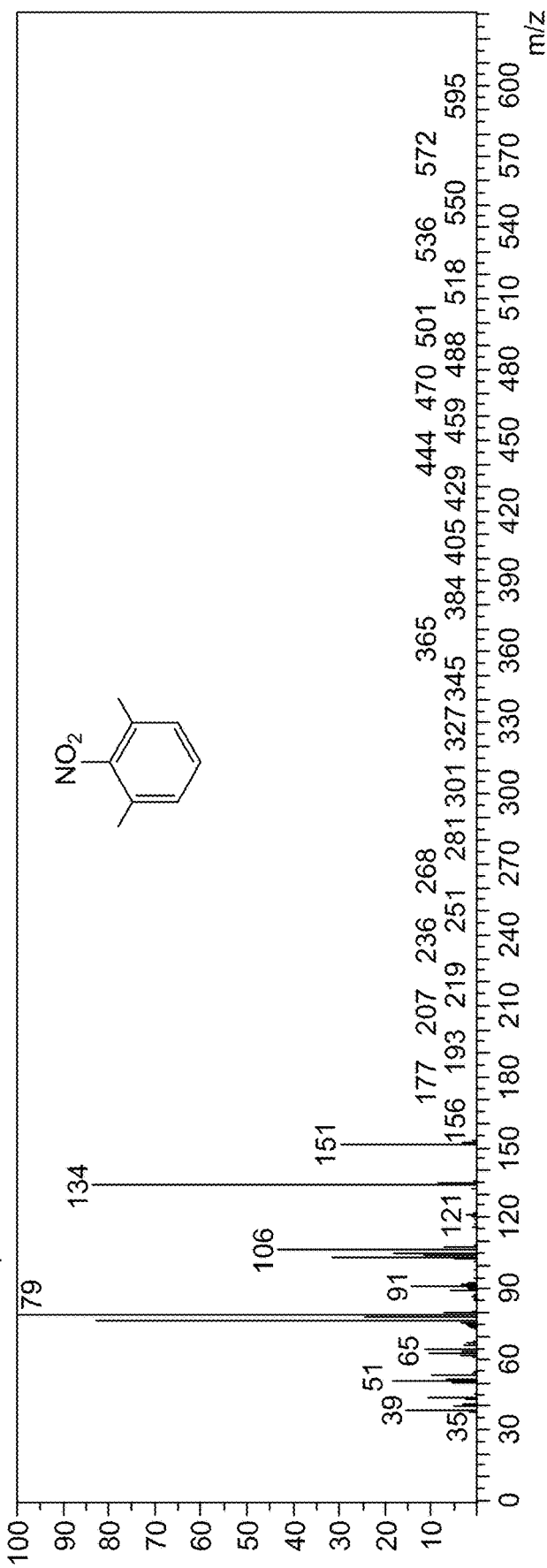
FIG. 22C is a mass spectrum identifying 1,3-dimethyl-2-nitrobenzene.

The leaching of the catalytic rhodium from the supported catalyst of the present disclosure into the reaction mixture is minimal (see FIG. 15B) and thus the supported catalyst may be recycled and reused without much loss in the catalytic activity. In one or more embodiments, the process of the present disclosure further involves the steps of separating the supported catalyst from the aromatic amine compound, and reusing the supported catalyst.

The reaction mixture is preferably heterogeneous and comprises suspended supported catalyst particles in a liquid reaction mixture. In one embodiment, the supported catalyst particles are dispersed within the reaction mixture, and may further be collected and recycled at the end of the reaction. Preferably, the supported catalyst is separated from the products via external magnetic extraction. Alternatively, the supported catalyst may be separated by using a micro-filter or a paper filter.

The phrase "reusing the catalyst" refers to a process whereby the supported catalyst is washed by an organic solvent, dried, and then added to a new batch of reactants (either for the same or a different type of reactant). Preferred organic solvents for washing the supported catalyst include, but are not limited to, methanol, acetone, ethanol, tetrahydrofuran, acetonitrile, dichloromethane, ether, glycol ether, acetamide, dimethyl acetamide, dimethyl sulfoxide, water, or combinations thereof. The supported catalyst may be dried in vacuum (e.g., at a reduced pressure of 0.01-100 mbar, 0.1-50 mbar, or 1-10 mbar), and/or with heating, for example, the supported catalyst may be dried in a vacuum oven. Dried supported catalyst may be stored in a desiccator until the next run.

In one embodiment, the supported catalyst is recovered and reused for at least 2 reaction iterations, preferably at least 3, preferably at least 4, preferably at least 5, preferably at least 10, preferably at least 20 reaction iterations. In some embodiments, the supported catalyst may be used continuously for 1-60 days, 2-40 days, 5-30 days, or 10-20 days. The supported catalyst may lose less than 5 wt %, preferably less than 2 wt %, more preferably less than 1 wt %, even more preferably less than 0.1 wt % of rhodium (based on an initial amount of rhodium present in the supported catalyst) after the catalyst is used for several iterations or several days. The yield of the catalyzed reduction reaction in converting the aromatic nitro compound to the aromatic amine may decrease less than 10%, preferably less than 5%, more preferably less than 1% after the supported catalyst is used for several iterations or several days (see FIG. 15A).

The examples below are intended to further illustrate protocols for preparing and characterizing the supported catalyst, and uses thereof. They are not intended to limit the scope of the claims.

Example 1

Materials and Methods

All chemicals were purchased from Sigma-Aldrich and used as received unless otherwise stated. Standard procedures were followed for drying and deoxygenating the solvents. Schlenk line techniques were used to carry out reactions under inert atmosphere wherever needed. Deionized (DI) water (specific conductivity: 18.2 mΩ) was used in all the experiments. Fourier-Transform Infrared (FTIR) spectroscopic data were obtained on a Nicolet 720 in the wave number range of 500 to 4000 cm$^{-1}$, using KBr as the IR transparent window material. X-ray diffraction data were collected on Rigaku model Ultima-IV diffractometer employing Cu-Kα radiation (λ=1.5405 Å) at 40 kV and 25 mA over a 2θ range between 20 and 90°. The Transmission Electron Microscopy images were acquired at the Instituto de Nanociencia de Aragón (LMA-INA), University of Zaragoza, Spain, on a TEM (Joel, J E M 2011) operated at 200 kV with 4 k×4 k CCD camera (Ultra Scan 400SP, Gatan) and at KFUPM in Transmission electron microscope JEM2100F from JEOL. The TEM samples were prepared by dropping on a copper grid from an ethanolic suspension and drying at room temperature. The amount of Rh in the catalyst was determined by Inductively Coupled Optical Emission Spectrometry (ICP-OES; PlasmaQuant PO 9000—Analytik Jena). The samples were first digested in a dilute mixture of $HNO_3$ and HCl. Calibration curves were prepared for Rh and Fe using standard solutions (ICP Element Standard solutions, Merk). Samples for Scanning Electron Microscopy (SEM) were prepared from ethanolic suspensions on alumina stubs and coated with gold in an automatic gold coater (Quorum, Q150T E). For the elemental analysis and mapping, the energy dispersive X-ray spectra (EDS) were collected on a Lyra 3 attachment to the SEM. The magnetic susceptibilities were measured at room temperature using a vibrating sample magnetometer (VSM, model PMC Micromag 3900) equipped with a 1 tesla magnet. Catalytic products were identified by a Shimadzu 2010 Plus (Japan) gas chromatograph attached with a mass spectrometer. The disappearance of the reactant and sequential appearance of the product was recorded in real-time, identifying the species in terms of their molecular ion (Mt) by comparing and matching them with the available Willey library of the mass spectrum database, in addition to the identification of mass fragmentation.

Example 2

Synthesis of Rh@$Fe_3O_4$ Catalyst

Magnetite ($Fe_3O_4$) nanoparticles with a particle size in the range of 8-10 nm were prepared according to a procedure described in the literature [M. N. Shaikh, M. Bououdina, A. A. Jimoh, M. A. Aziz, A. Helal, A. S. Hakeem, Z. H. Yamani, T.-J. Kim, New J. Chem. 39 (2015) 7293-7299, incorporated herein by reference in its entirety]. Nanoscale $Fe_3O_4$ powder (200 mg) was suspended in dry methanol (30 mL) and sonicated for 4 h to form a homogeneous suspension of magnetite. 100 µL of rhodium(III) nitrate solution (1.0×10$^{-4}$ mol, 0.09 g of Rh) was added to the homogeneous suspension of magnetite and stirred at 80° C. for 3 h under argon atmosphere. Concentrated $NH_4OH$ (27 M) was added to achieve and maintain a pH >12 within the mixture for 4 h. Particles were settled down by means of an external magnet. They were washed with a copious amount of water followed by dichloromethane. Following the above same procedure of catalyst 1a (4.2 wt % Rh), catalyst 1b (6.5 wt % Rh), and 1c (8.2 wt % Rh) were prepared.

Example 3

Procedure for Catalytic Reduction

The catalytic reduction of nitrophenol was performed in a parallel 10-place reaction tube reactor fitted with a magnetic stirrer and a Teflon stopper. To the Rh@$Fe_3O_4$ (5 mg) suspension in deionized water (2 mL), nitrophenol (0.5 mmol, 69 mg) was added and the system was flushed with argon gas three times. Tetrahydroxydiboron (4 mmol) was added, capped with Teflon stopper and heated to 60° C. Progress of the reaction was monitored by TLC (thin layer chromatography). The product was extracted with ethyl acetate (EA) and dried with sodium sulphate. It was passed through a short silica gel column using EA and hexane (6:4) mixture as an eluent. Conversion was measured by GC and identified by the GC-MS system.

Example 4

Synthesis and Characterization of Catalysts

As a part of an on-going effort [M. N. Shaikh, M. Bououdina, A. A. Jimoh, M. A. Aziz, A. Helal, A. S. Hakeem, Z. H. Yamani, T.-J. Kim, New J. Chem. 39 (2015) 7293-7299; M. N. Shaikh, M. A. Aziz, A. Helal, M. Bououdina, Z. H. Yamani, T.-J. Kim, RSC Adv. 6 (2016) 41687-41695; and M. N. Shaikh, M. A. Aziz, A. Helal, A. N. Kalanthoden, Z. H. Yamani, ChemistrySelect 2 (2017) 9052-

9057, each incorporated herein by reference in their entirety], catalysts were prepared by loading various amount of Rh on magnetite nanoparticles suspended in water, via an in-situ reduction using aqueous ammonia. The preparation involves aqueous and alkaline media at an elevated temperature. The stability of the catalyst also lowers the probability of leaching of Rh constructed on the magnetic nanoparticles, which was evidenced by reaffirming the ratio of Fe/Rh in the catalysts after subjecting them to vigorous sonication.

Figure 1B:
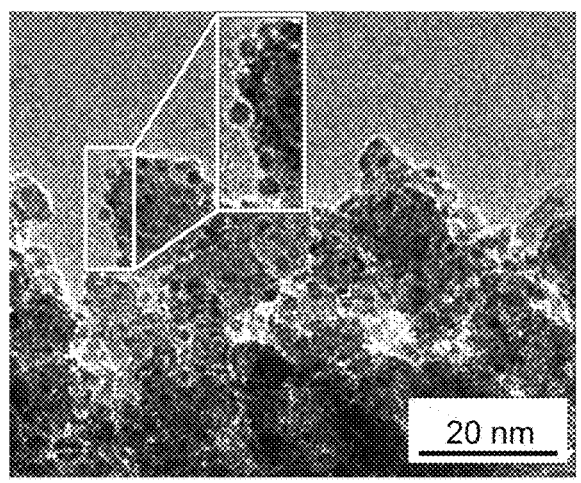
FIG. 1B is a TEM image of supported catalyst 1b (6.5 wt % Rh@$Fe_3O_4$) with a magnified view inset showing rhodium subnanoparticles decorated on $Fe_3O_4$ particles.
Figure 1C:
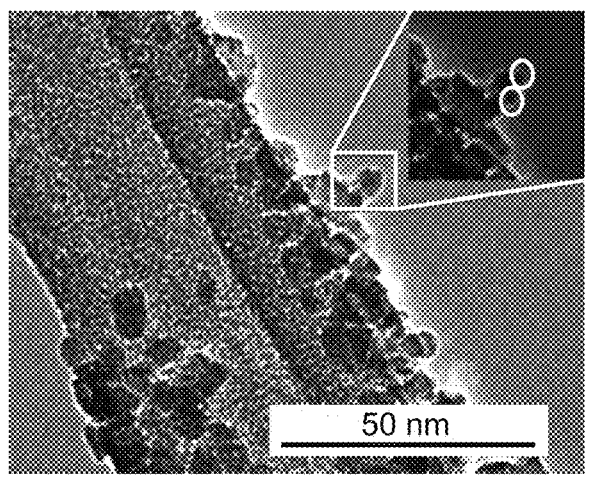
FIG. 1C is a TEM image of supported catalyst 1c (8.2 wt % Rh@$Fe_3O_4$) with a magnified view inset showing rhodium subnanoparticles decorated on $Fe_3O_4$ particles.
Figure 3A:
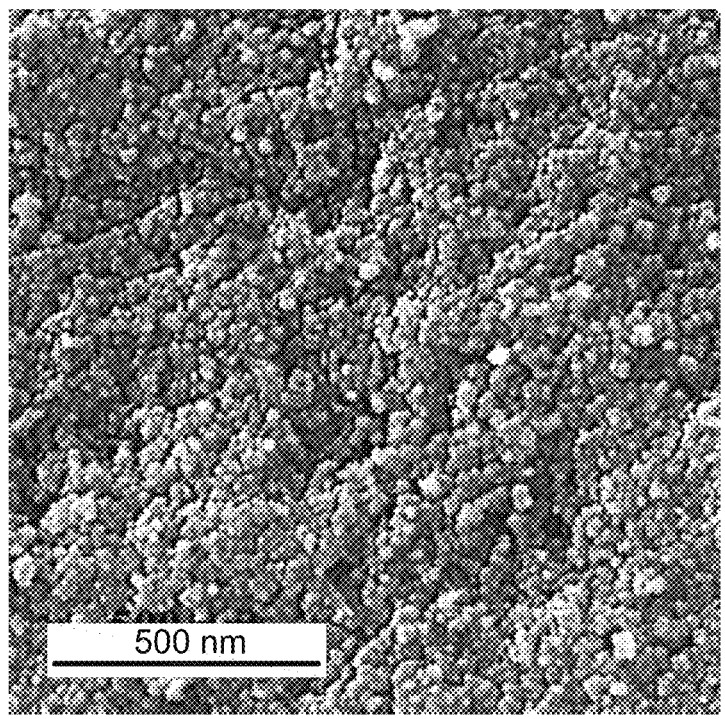
FIG. 3A is a scanning electron microscope (SEM) image of catalyst support $Fe_3O_4$.
Figure 3B:
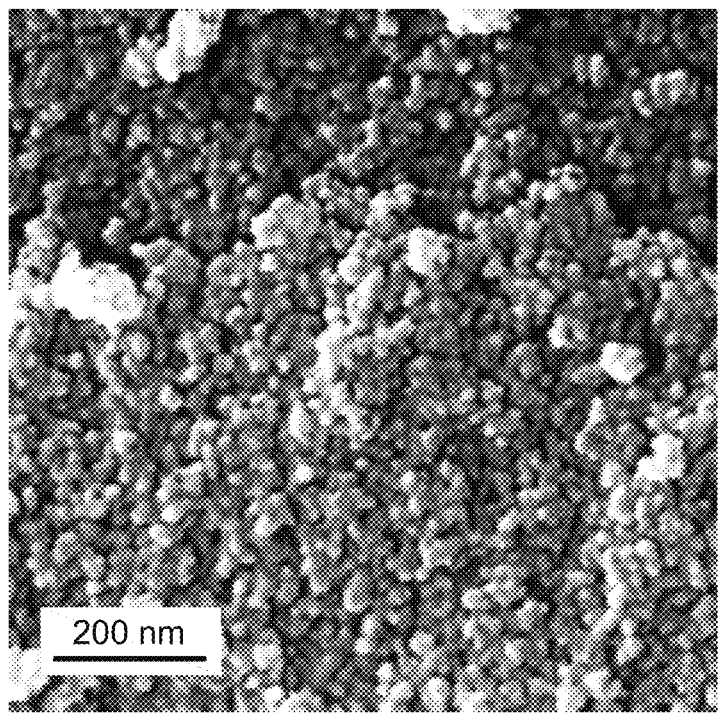
Figure 3C:
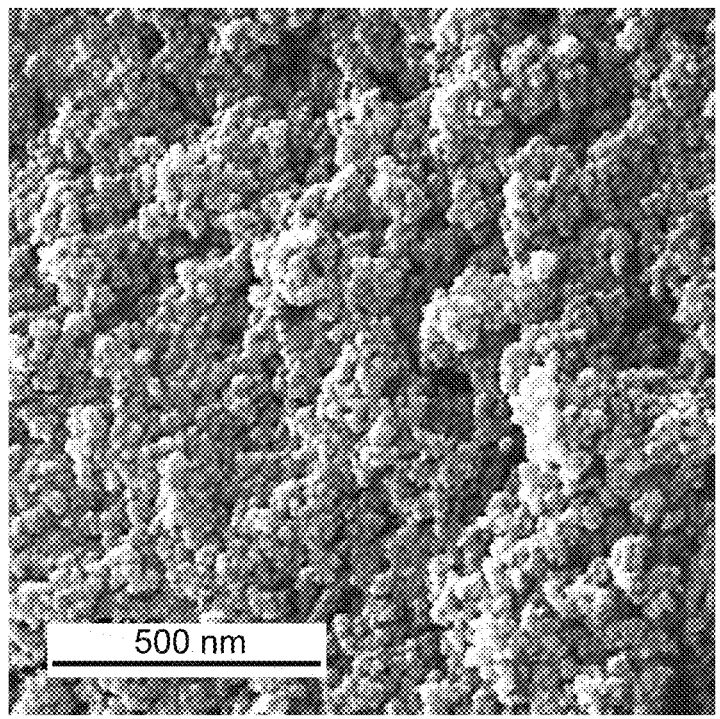
FIG. 3C is a SEM image of supported catalyst 1b.
Figure 3D:
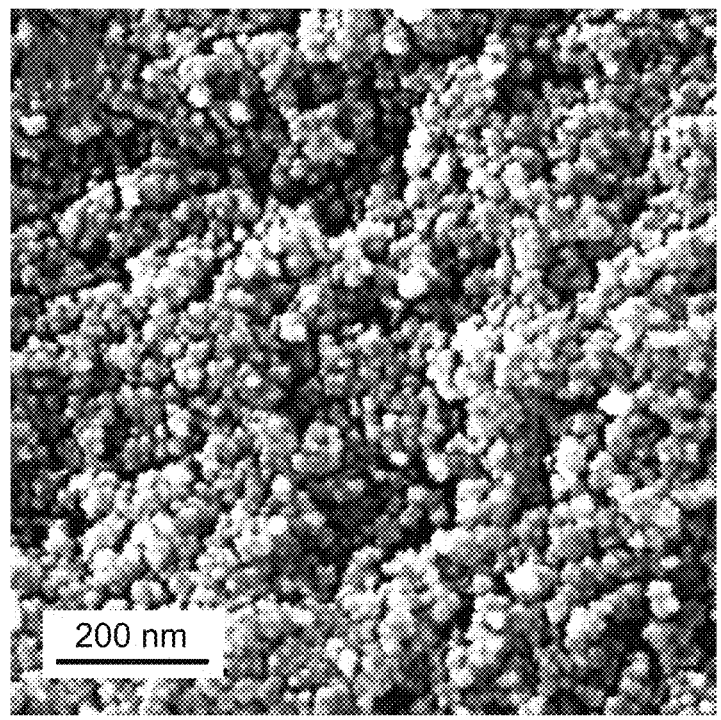
FIG. 3D is a SEM image of supported catalyst 1c.
Figure 4A:
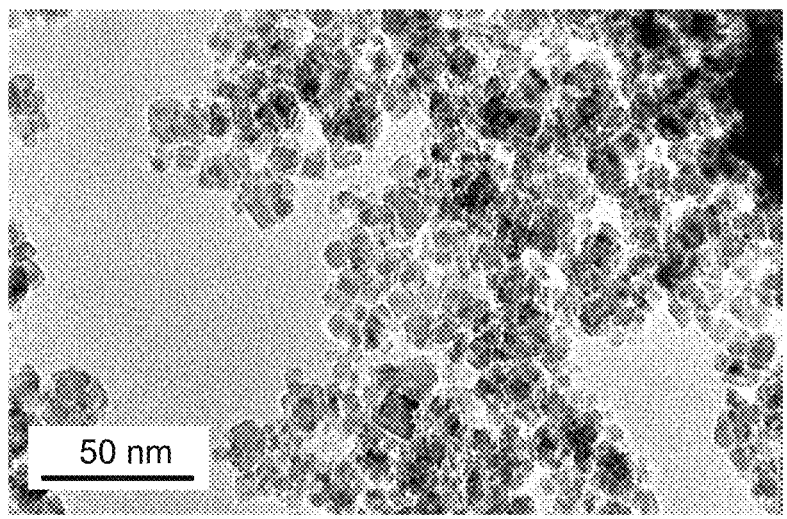
FIG. 4A is a TEM image of catalyst support $Fe_3O_4$.
Figure 4B:
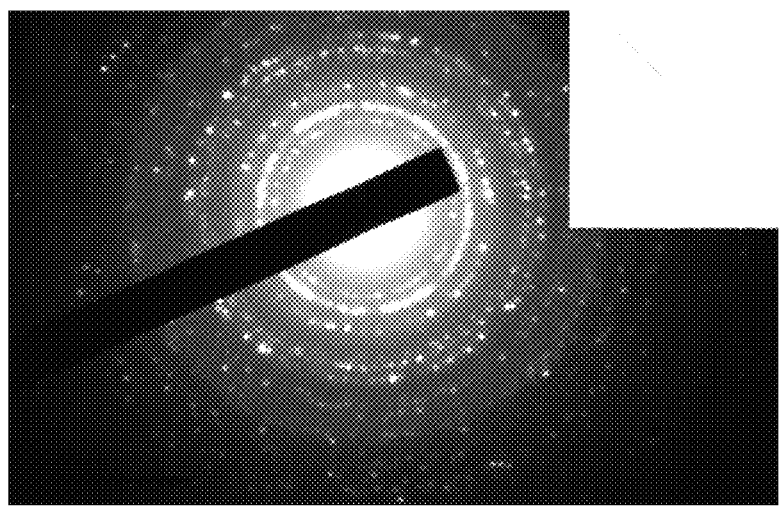
FIG. 4B is a selected area electron diffraction pattern of supported catalyst 1c.
Figure 4C:
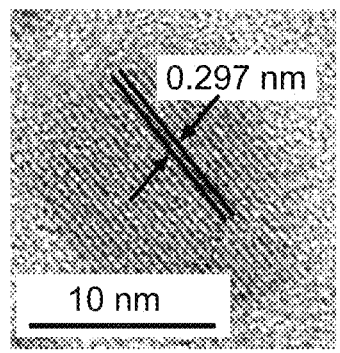
FIG. 4C is a high resolution TEM (HRTEM) image of supported catalyst 1c.
Figure 5A:
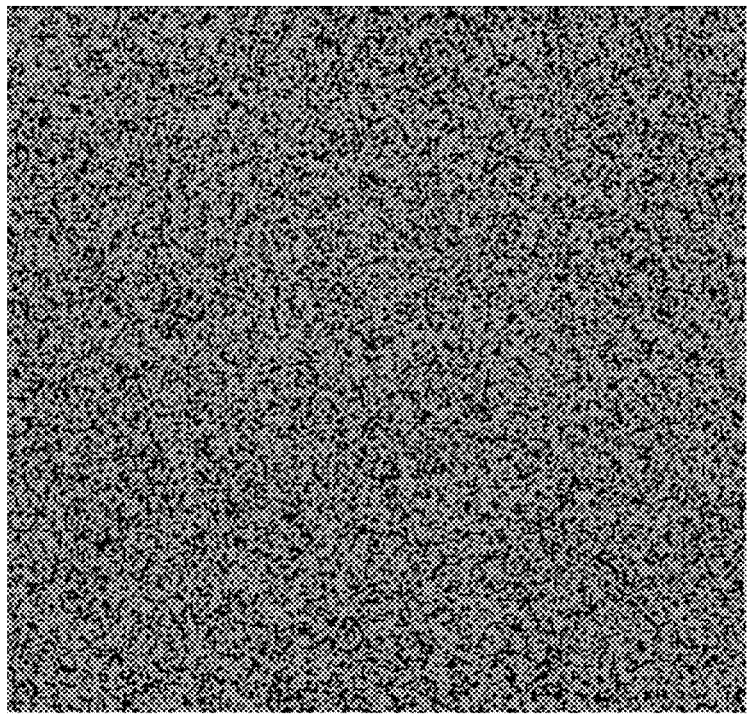
Figure 5B:
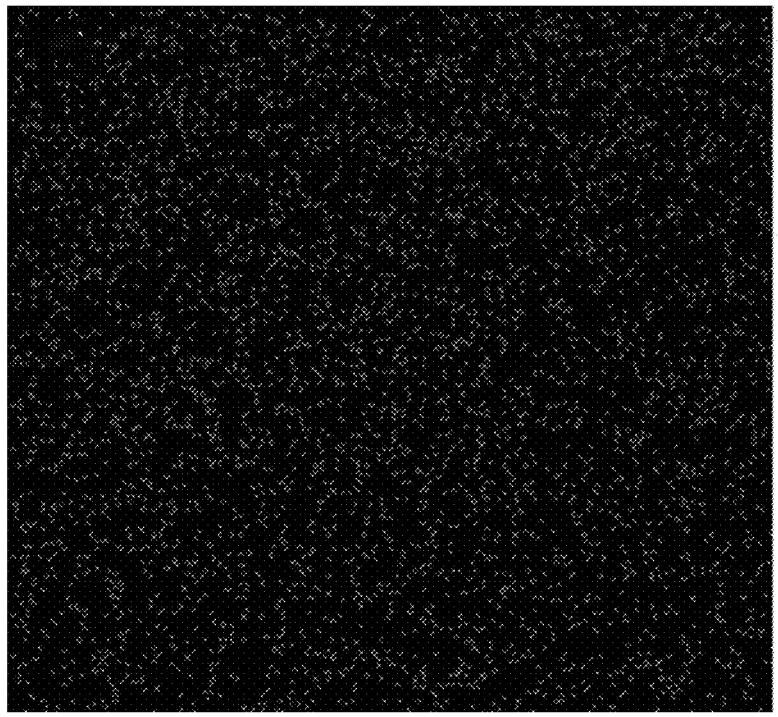
Figure 6A:
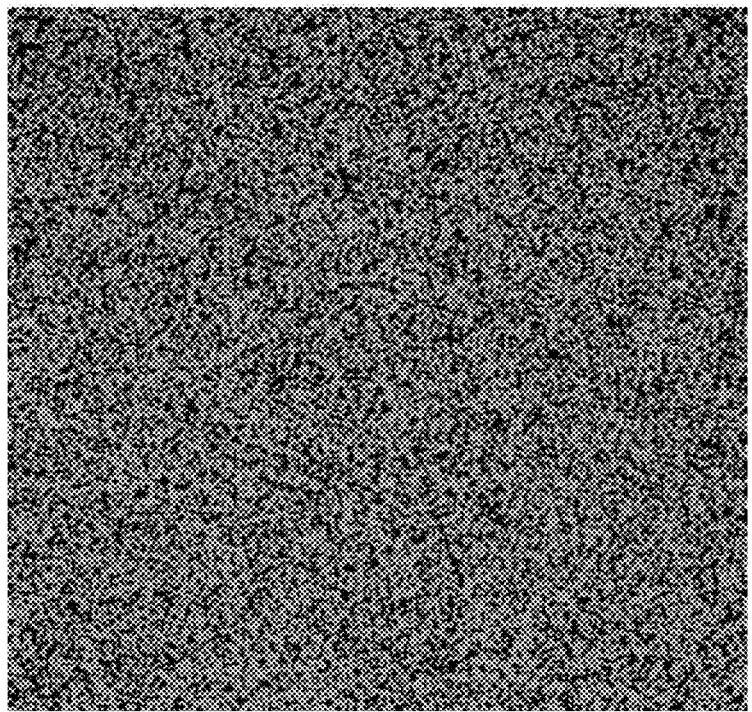
FIG. 6A is an elemental mapping of iron of supported catalyst 1c.
Figure 6B:
FIG. 6B is an elemental mapping of rhodium of supported catalyst 1c.
Figure 7A:
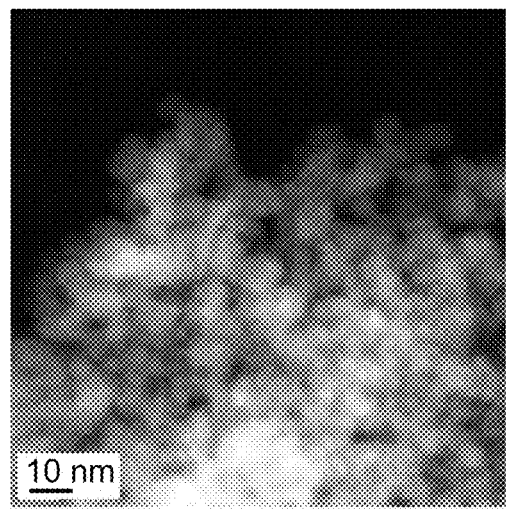
Figure 7B:
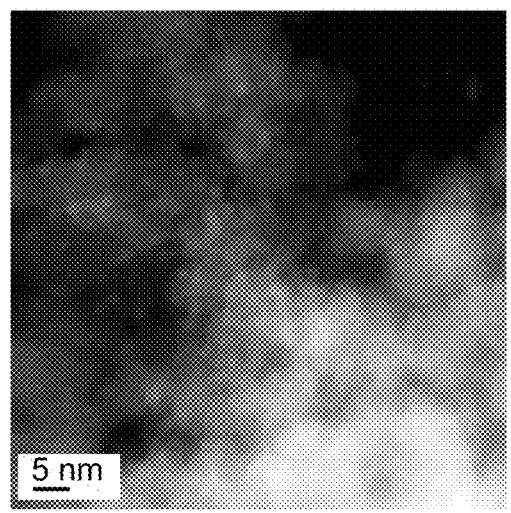
FIG. 7B is a STEM image of supported catalyst 1b.
Figure 7C:
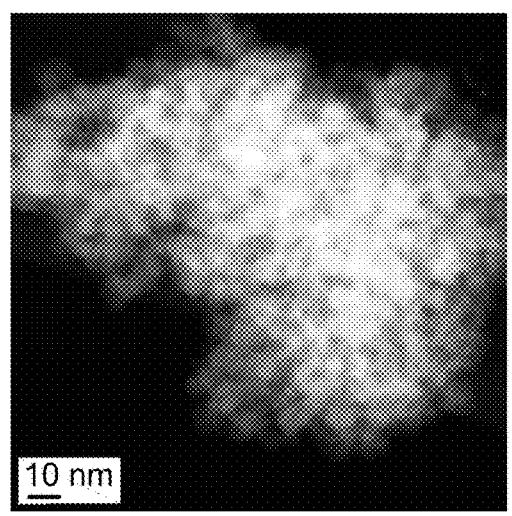
FIG. 7C is a STEM image of supported catalyst 1c.
Figure 8A:
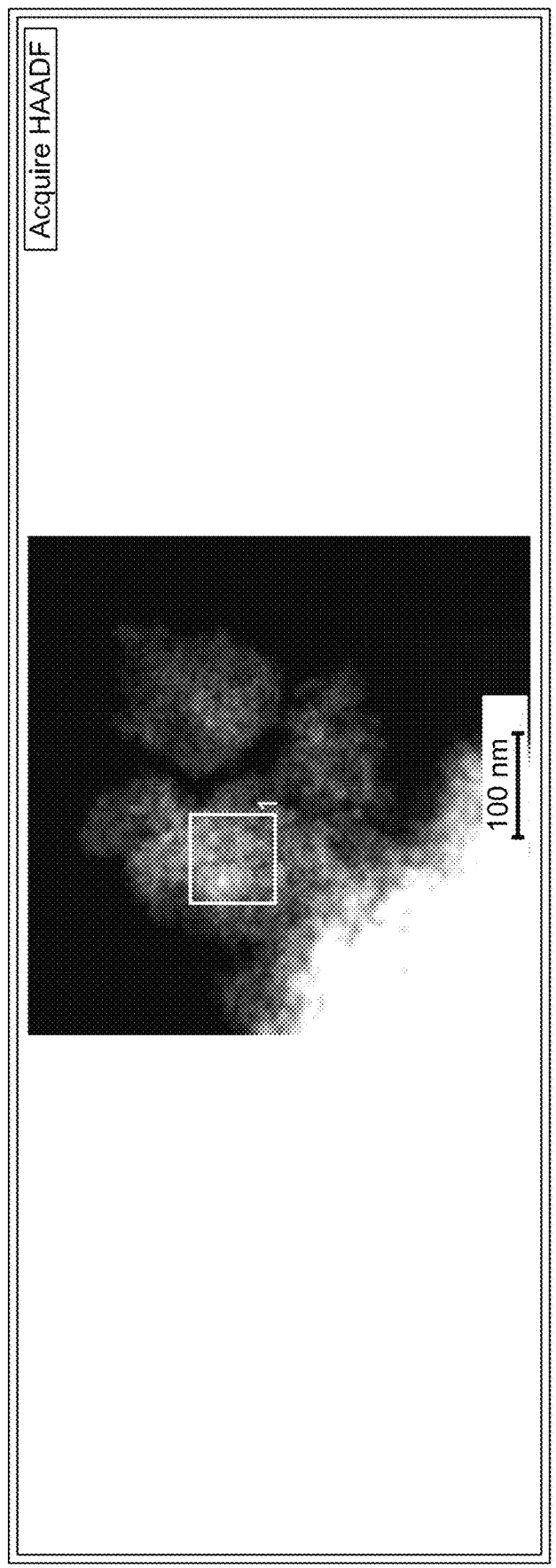
Figure 8B:
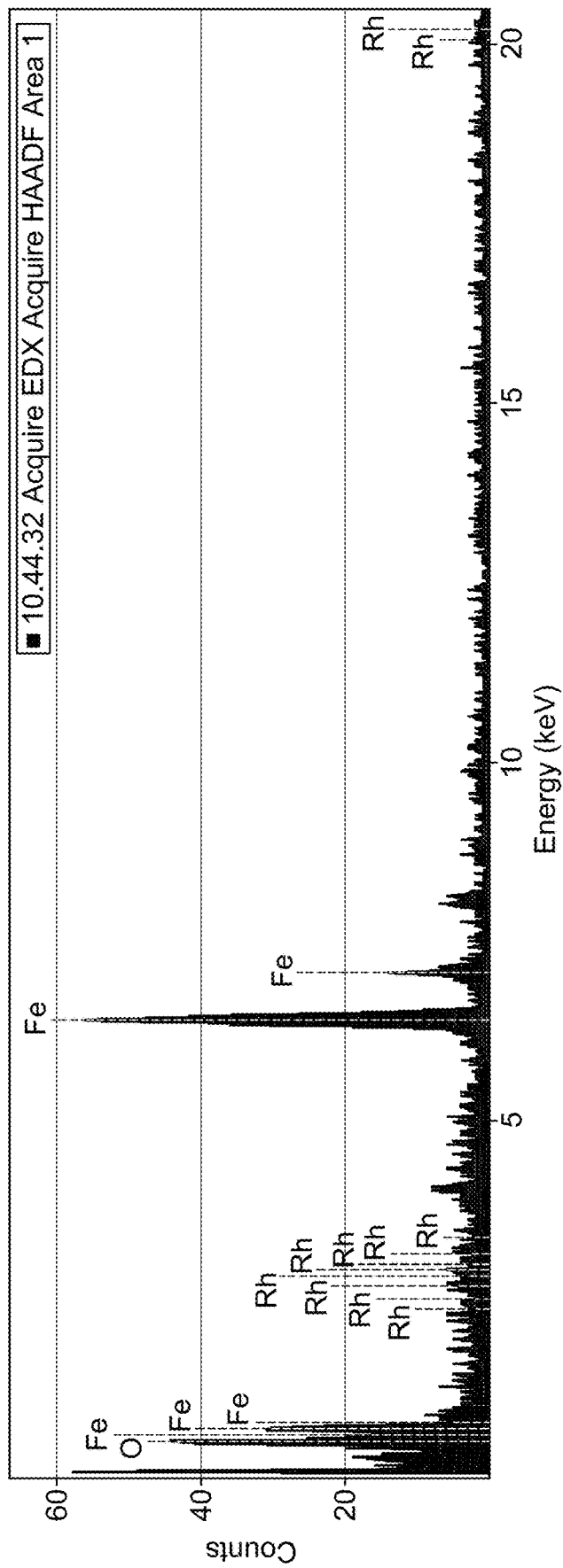
Figure 9A:
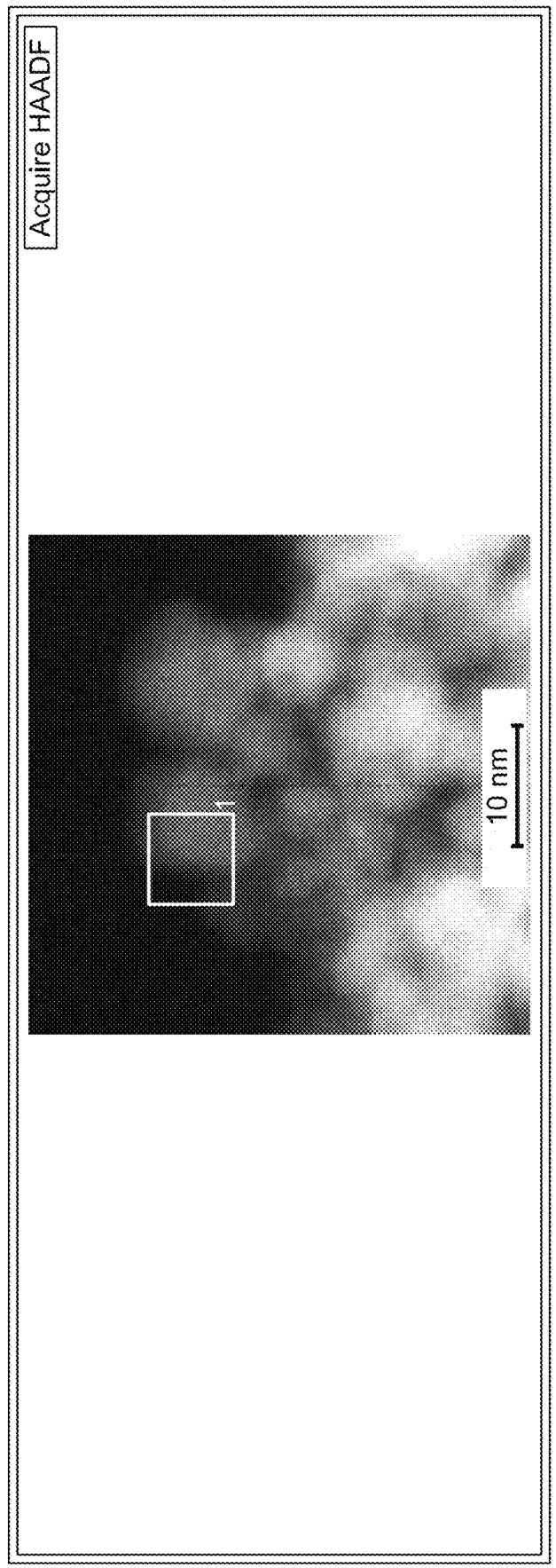
FIG. 9A is a STEM image of supported catalyst 1b.
Figure 9B:
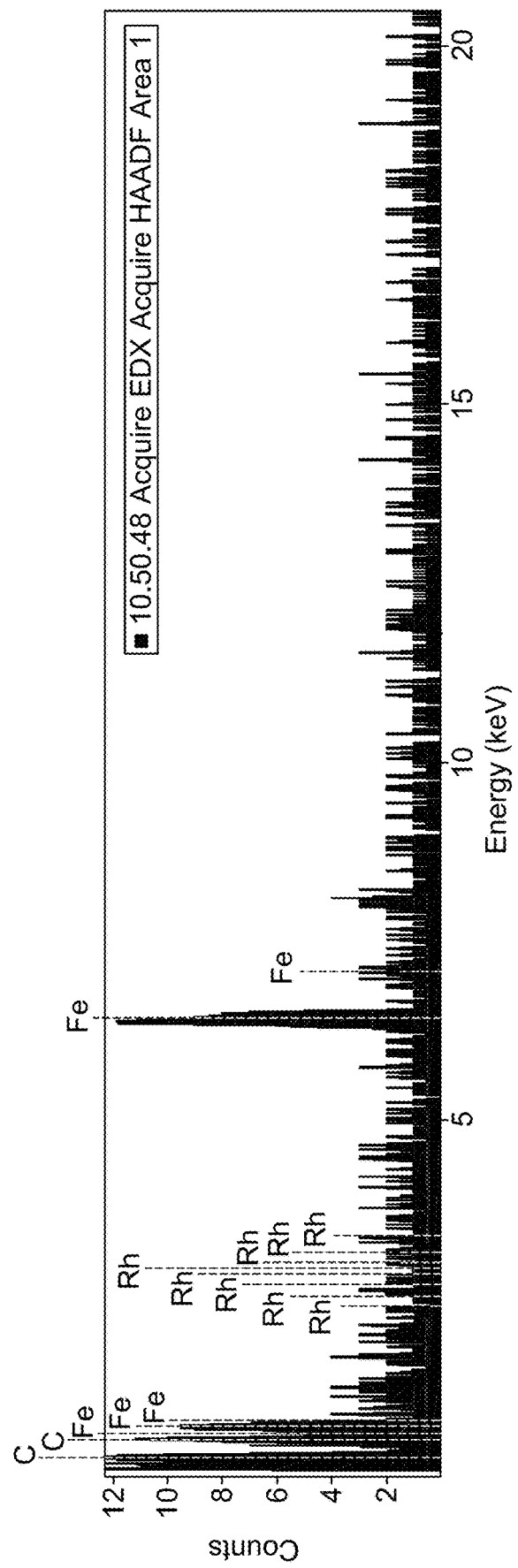
FIG. 9B is an EDS spectrum of supported catalyst 1b.
Figure 10A:
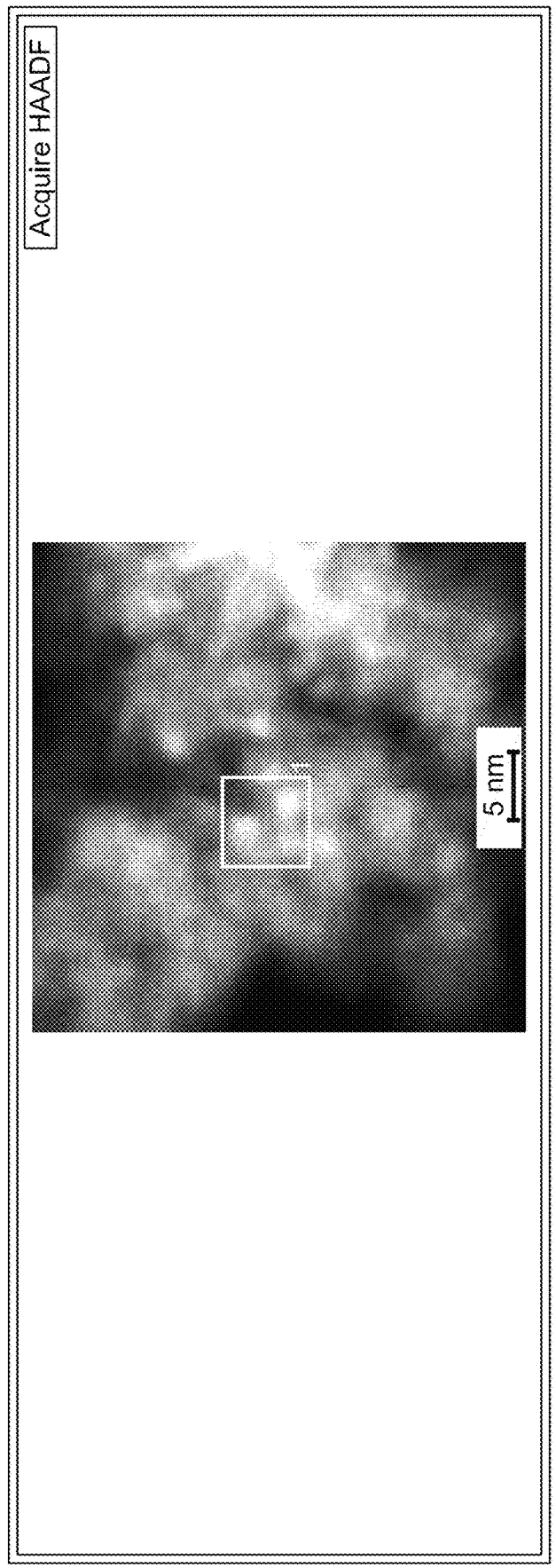
FIG. 10A is a STEM image of supported catalyst 1c.
Figure 10B:
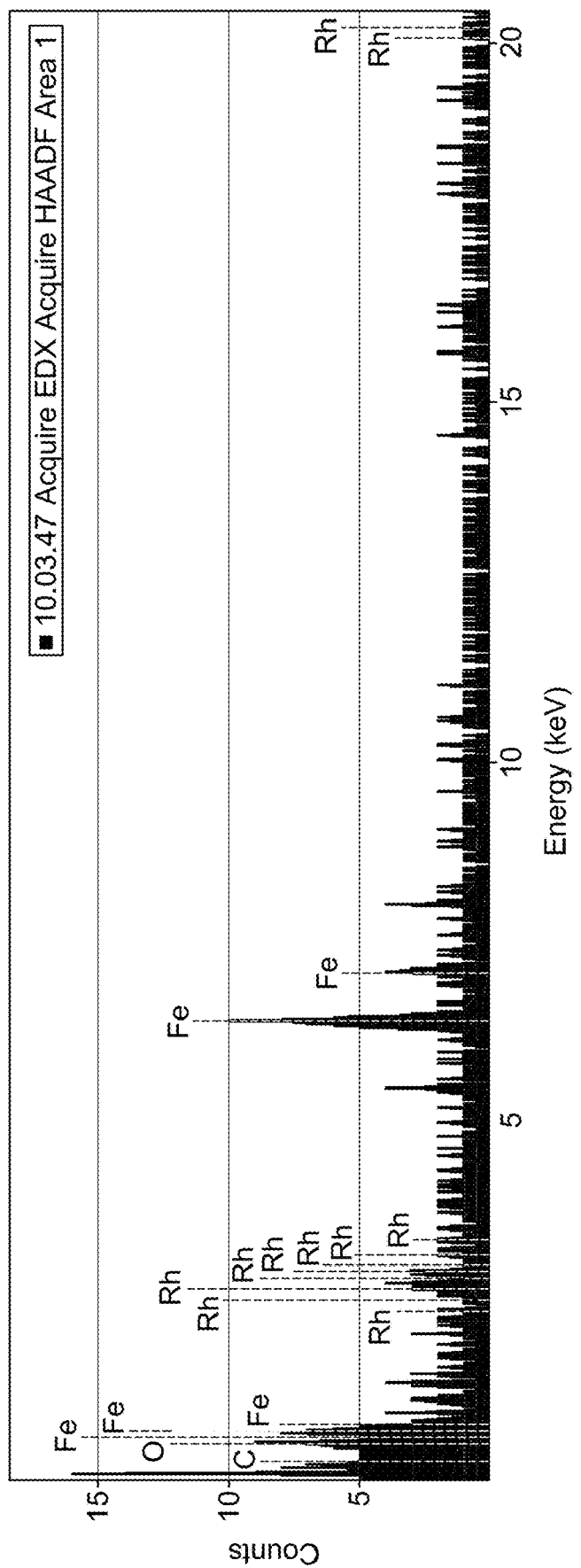
FIG. 10B is an EDS spectrum of supported catalyst 1c.

Transmission electron microscopy (TEM) revealed a homogeneous distribution of spherical pure magnetite nanoparticles with an average particle size in the range of 8-10 nm (see FIGS. 3A and 4A). A uniform and homogeneous distribution of Rh on magnetite particles is evident from FIGS. 1A-C. The lattice fringe d-spacing computed from the HRTEM image is 0.297 nm, corresponding to the <220> plane of $Fe_3O_4$. The selected area electron diffraction (SAED) spectrum is indicative of high crystallinity of the magnetite particles (see FIG. 4B). The TEM micrograph (FIGS. 1A-C) of the catalyst demonstrates the presence of well-dispersed spherical nanostructured magnetite particles. Furthermore, the magnetite surface was evenly decorated with Rh particles (<1 nm), which was confirmed by the confined area elemental mapping of Fe and Rh, indicating a homogenous distribution of Rh over the selected frame (see FIGS. 5A-B, 6A-B). The identity and ultra-small dimension of Rh (<1 nm) were confirmed by scanning transmission electron microscopy (STEM) (see FIGS. 7A-C, 8A-B, 9A-B, 10A-B). Amounts of Rh loading on different catalysts were determined to be 4.2, 6.5 and 8.2 wt %, which were corroborated well by studies using ICP-OES.

Figure 11:
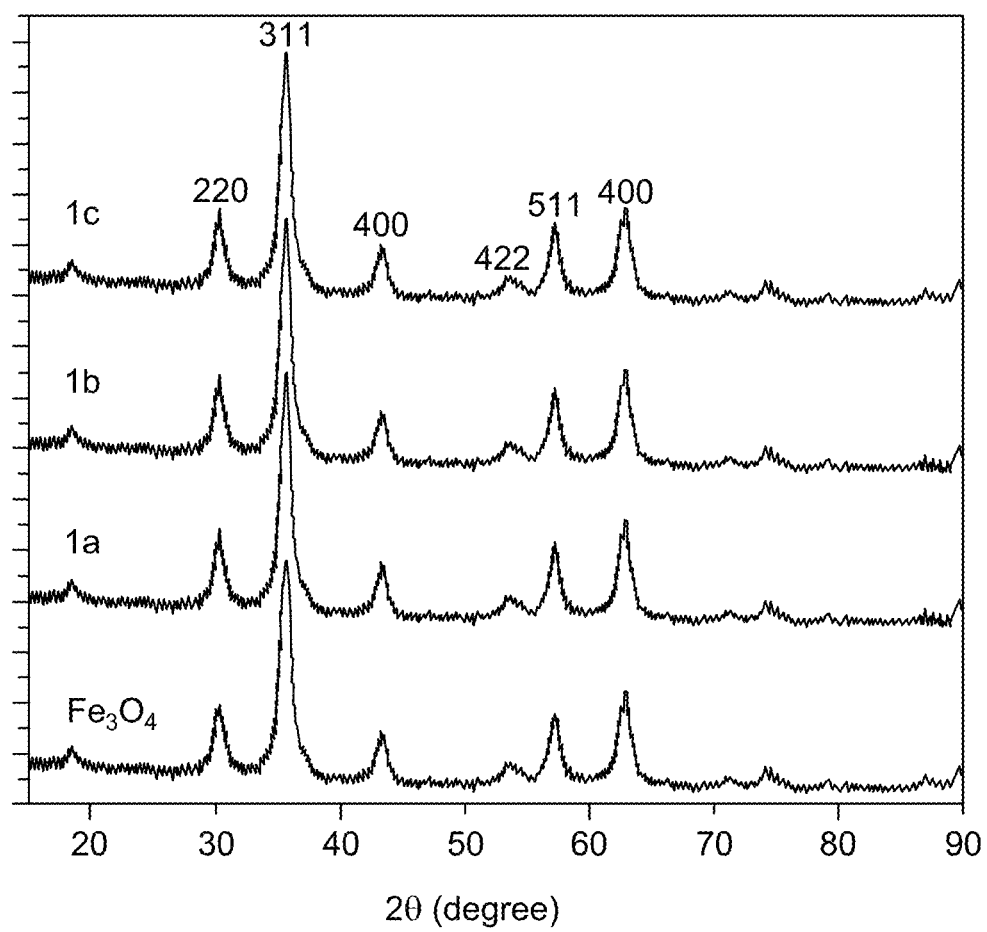
FIG. 11 is an overlay of X-ray diffraction (XRD) patterns of catalyst support $Fe_3O_4$, and supported catalysts 1a, 1b, and 1c.
Figure 12A:
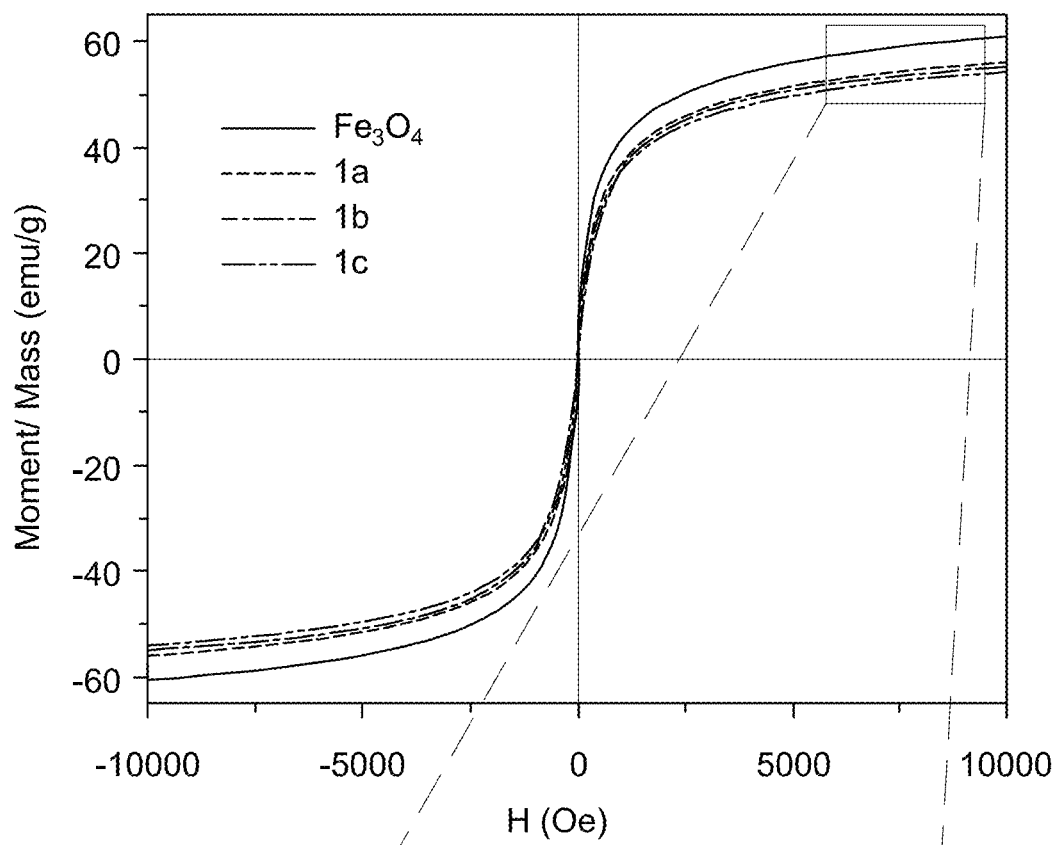
FIG. 12A is an overlay of magnetic moment-magnetic field (B—H) hysteresis loops of catalyst support $Fe_3O_4$, and supported catalysts 1a, 1b, and 1c.
Figure 12B:
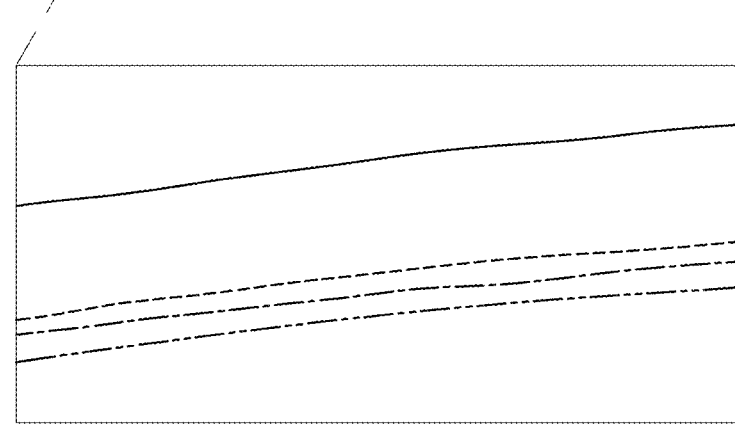
FIG. 12B shows a magnified view of magnetic saturation ($M_s$) data of catalyst support $Fe_3O_4$, and supported catalysts 1a, 1b, and 1c.
Figure 13A:
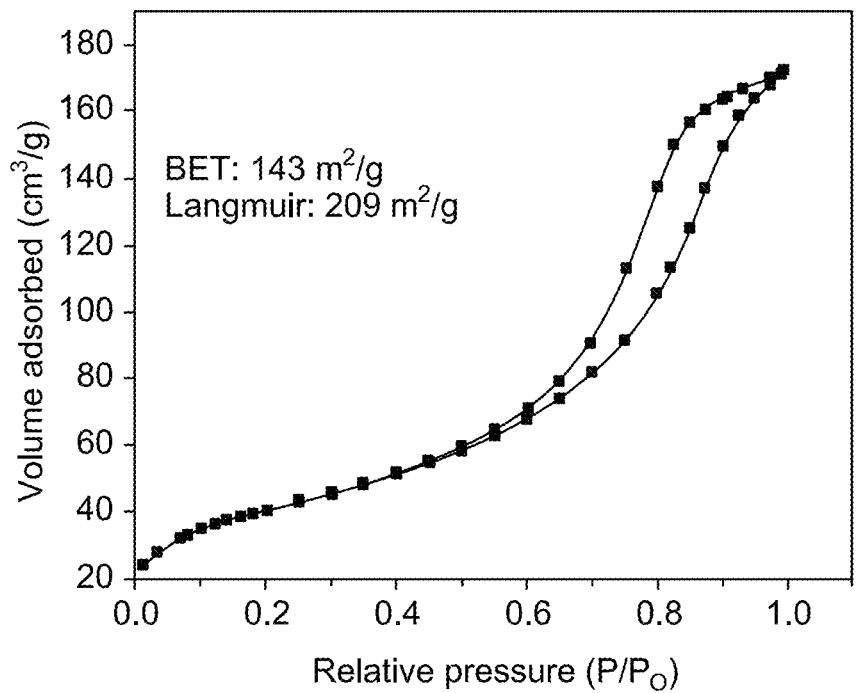
FIG. 13A shows $N_2$ gas adsorption isotherms of catalyst support $Fe_3O_4$.
Figure 13B:
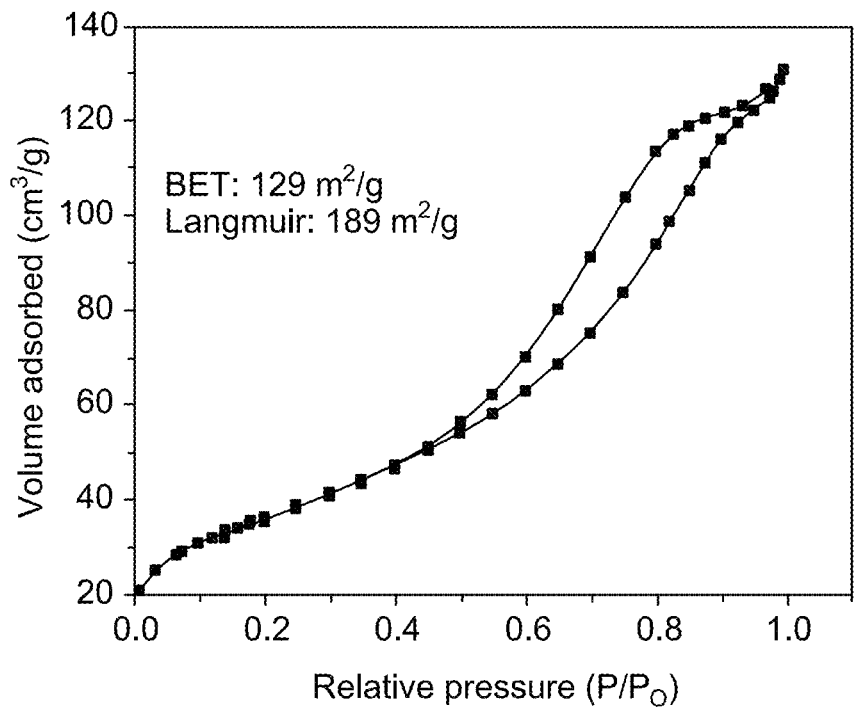
Figure 13C:
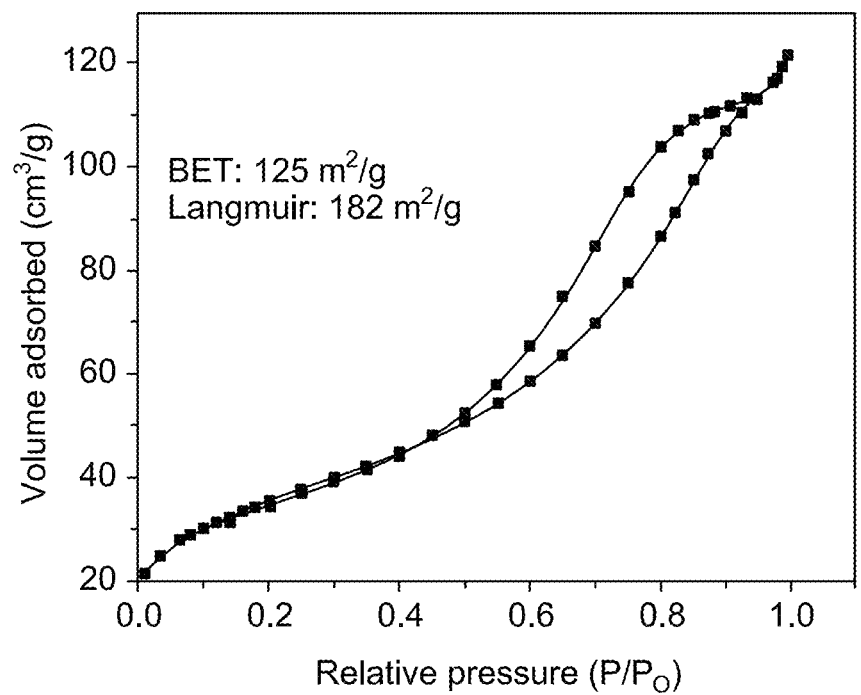
FIG. 13C shows $N_2$ gas adsorption isotherms of supported catalysts 1b.
Figure 13D:
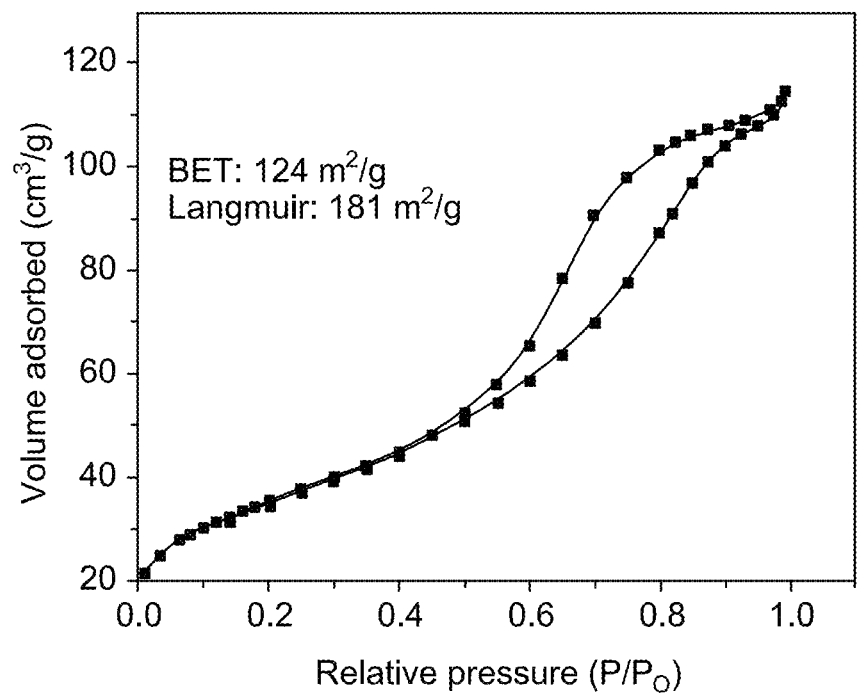
FIG. 13D shows $N_2$ gas adsorption isotherms of supported catalysts 1c.

The crystal structures of pure $Fe_3O_4$ and $Rh@Fe_3O_4$ series were further investigated (see FIG. 11). Broad diffraction peaks at 2θ=30.22, 35.70, 43.10, 53.40, 57.10 and 63.20° indicate a formation of nanocrystalline $Fe_3O_4$ in cubic (Fd3m) spinel structure (ICCD card No. 01-075-0449). Incorporation of different amounts of Rh at nanoscale did not affect the parent crystal structure as evident from XRD (FIG. 1d). This was corroborated by the B—H curves for pure and Rh-supporting magnetite particles (see FIG. 12). It has been shown that the value of coercivity ($H_c$) was within the range of 3.82 to 0.842. Similarly, the saturation magnetization ($M_s$) value slightly decreased from 60.68 to 54.05 emu $g^{-1}$, which might be due to surface decoration. It is also clear that surface decoration is minutely affecting the bulk magnetization, since the $Rh@Fe_3O_4$ particles were still magnetic enough to be separated using a simple magnet.

FTIR spectroscopy was conducted to confirm the formation of composite $Rh@Fe_3O_4$ system. Peaks at 584 and 1420 $cm^{-1}$ could be ascribed to the bending and stretching vibrational modes of the Fe—O bond, respectively. A small peak at 1600 $cm^{-1}$ was attributed to the bending vibrational motion of water absorbed on the magnetite's highly polar surface. A broad peak around 3400 $cm^{-1}$ signifies the presence of coordinated hydroxyl groups [Z. Zarnegar, J. Safari, New J. Chem. 38 (2014) 4555-4565, incorporated herein by reference in its entirety]. Incorporation of Rh nanoparticles did not alter the IR spectra significantly.

Brunner-Emmet-Teller (BET) surface area measurements were carried out to determine the extent of exposed surface and porosity in pure and Rh-loaded $Fe_3O_4$ (see FIGS. 13A-D). Data revealed that the measured BET surface area decreased from 143 $m^2/g$ to 124 $m^2/g$ with increasing amount of Rh loading. The observed decrease in the surface area may be due to the blocking of some pores upon deposition of Rh on magnetite particles, which was confirmed by ICP-OES measurements.

Example 5

Catalytic Performance of $Rh@Fe_3O_4$

Figure 2A:
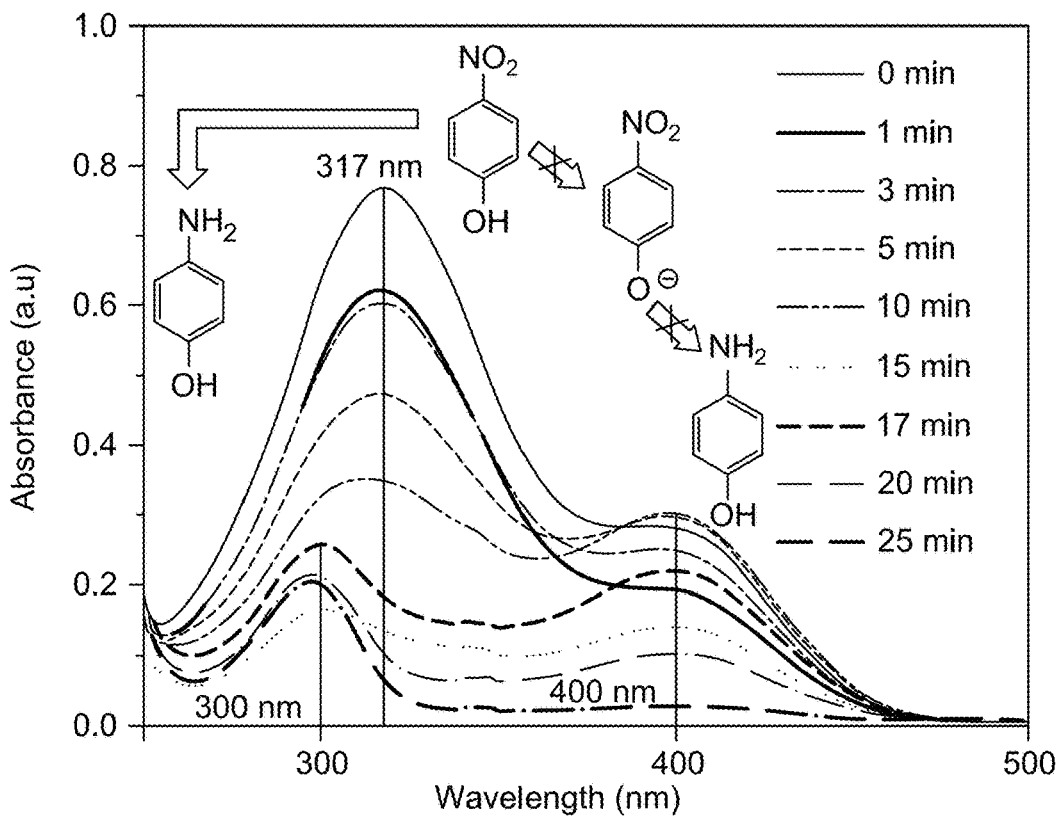
FIG. 2A shows an overlay of time-dependent UV-vis absorption spectra of aqueous phase reduction of 4-nitrophenol with tetrahydroxydiboron (THDB) in the presence of supported catalyst 1c at 40° C.
Figure 2B:
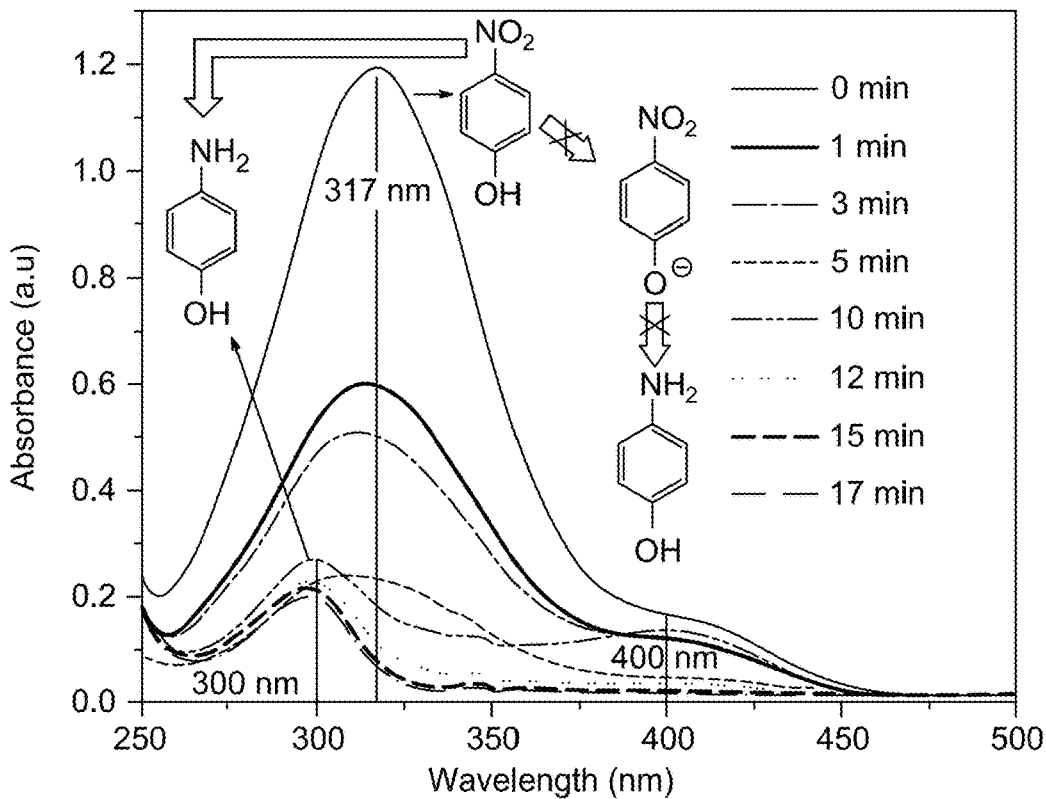
FIG. 2B shows an overlay of time-dependent UV-vis absorption spectra of aqueous phase reduction of 4-nitrophenol with THDB in the presence of supported catalyst 1c at 50° C.
Figure 2C:
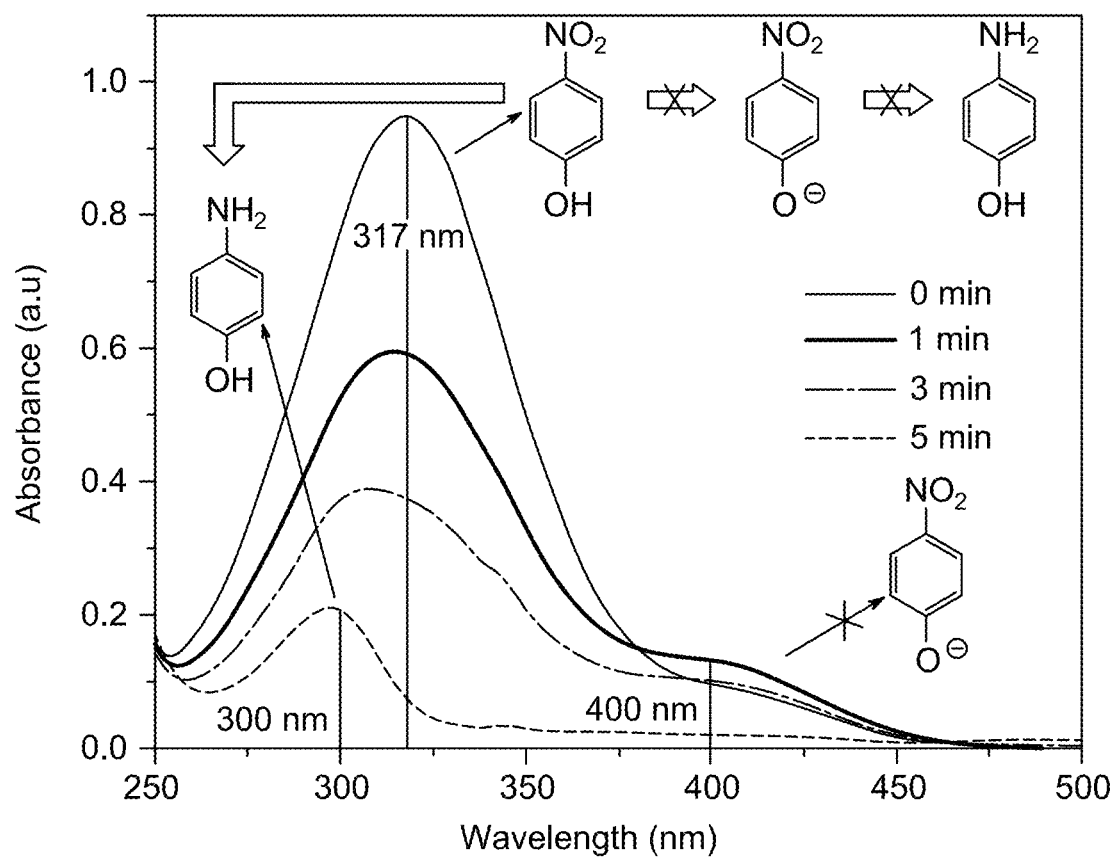
FIG. 2C shows an overlay of time-dependent UV-vis absorption spectra of aqueous phase reduction of 4-nitrophenol with THDB in the presence of supported catalyst 1c at 60° C.

To evaluate the performance of $Rh@Fe_3O_4$ catalysts in water, 4-nitrophenol (4-NP) was chosen as a model system and tetrahydroxydiboron as reducing agent. The reduction was monitored using UV-Vis absorption spectroscopy at 40-60° C. as a function of time, and results are shown in FIGS. 2A-C.

An absorption peak at 317 nm appeared at t=0 min at all temperatures, which shifted down upon the addition of THDB and decreased as reaction continued. Eventually the absorption peak appeared at 300 nm, indicating the catalytic reduction of 4-nitrophenol to 4-aminophenol. The reduction kinetics became faster as temperature increased from 40 to 60° C. At 40° C., a much lower amount of nitrophenolate formation was detected (FIG. 2a). However, when the temperature (FIGS. 2B and 2C) was increased to 60° C., no deprotonation of nitrophenol was observed and a quantitative conversion of 4-nitrophenol to 4-aminophenol took place in 5 min. This process is quite different from the conventional $NaBH_4$-mediated reduction, which proceeds via deprotonation of 4-nitrophenol to form 4-aminophenol [D. M. Dotzauer, J. Dai, L. Sun, M. L. Bruening, NanoLett. 6 (2006) 2268-2272, incorporated herein by reference in its entirety]. In fact, no conversion of aminophenol was observed with the $Rh@Fe_3O_4$ (1c) catalyst in the absence of THDB. This is also corroborated by the fact that <10% conversion was recorded with THDB but without the catalyst at 60° C. (Table 2, entry #6). Hence, a combination of $Rh@Fe_3O_4$ and THDB as a reductant favors the conversion process.

Since only aminophenol peak was observed in the UV-vis spectra, it is most likely that the reduction process follows the path involving a direct route. It is worth pointing out that reduction begins as soon as the catalyst is introduced without any induction period, though this is in contrast to what has been reported in the literature for the reduction of nitroaromatics using noble metals [K. Layek, M. L. Kantam, M. Shirai, D. Nishio-Hamane, T. Sasakid, H. Maheswaran, Green Chem. 14 (2012) 3164-3174; and Y. Lu, Y. Mei, M. Drechsler, M. Ballauff, Angew. Chem. Int. Ed. 45 (2006) 813-816, each incorporated herein by reference in their entirety]. This is most likely due to the preferential reaction of THDB with the nitro group of nitrophenol rather than with dissolved oxygen [S. Saha, A. Pal, S. Kundu, S. Basu, T. Pal, Langmuir 26 (2010) 2885-2293, incorporated herein by reference in its entirety]. Furthermore, catalysis of the present case was performed under ambient conditions, which is believed to be advantageous in the context of technological applications, as it does not require special environment handling. In addition, the hydrogen released from THDB purges out to the air, which further prevents aerial oxidation of 4-aminophenol.

Figure 14A:
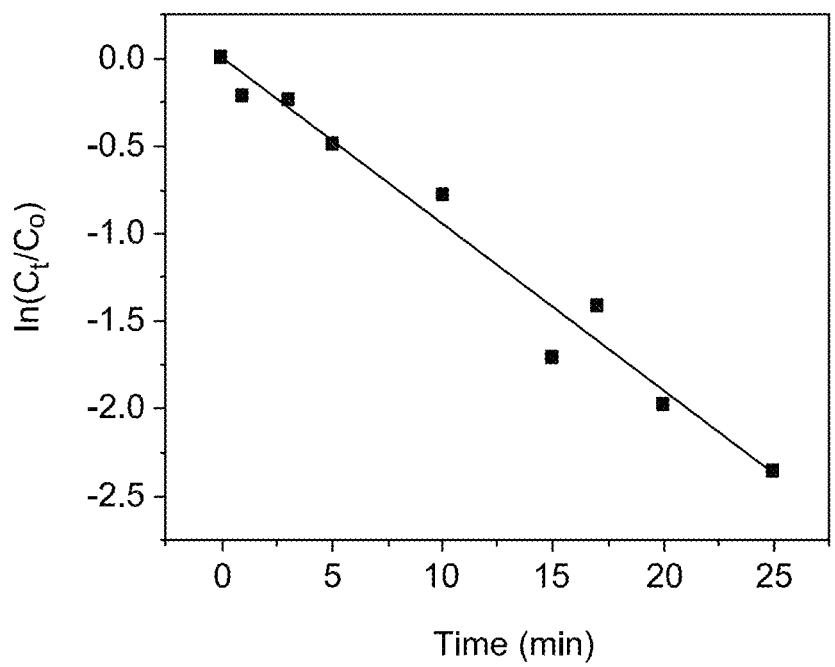
FIG. 14A is a kinetic plot for the reduction of 4-nitrophenol by THDB in the presence of supported catalyst 1c at 40° C.
Figure 14B:
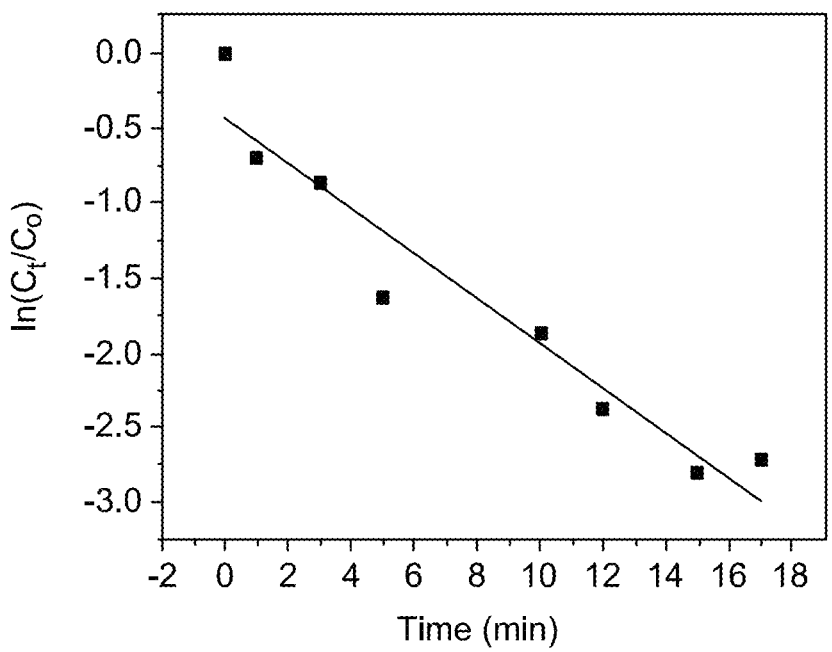
FIG. 14B is a kinetic plot for the reduction of 4-nitrophenol by THDB in the presence of supported catalyst 1c at 50° C.
Figure 14C:
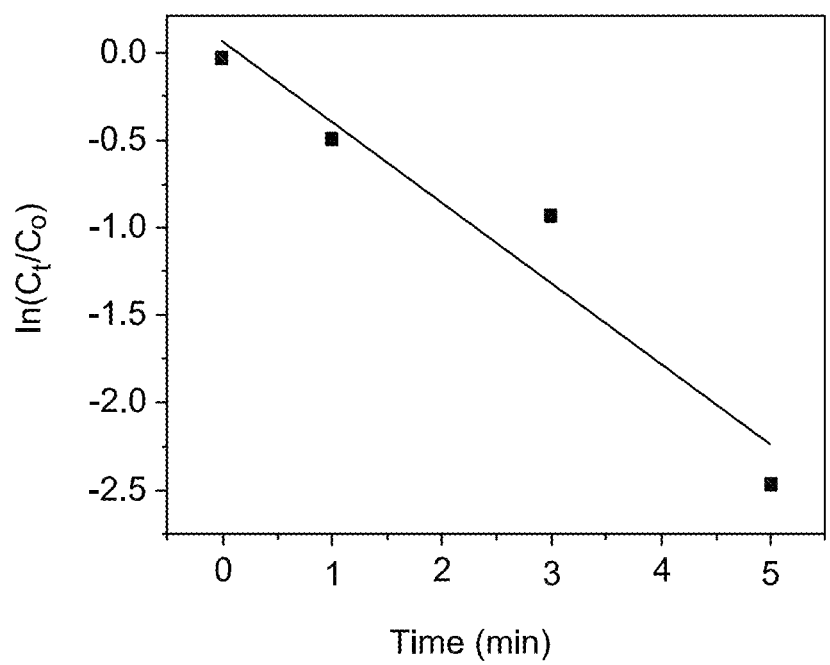
FIG. 14C is a kinetic plot for the reduction of 4-nitrophenol by THDB in the presence of supported catalyst 1c at 60° C.

The reaction rates were tested and calculated at different reaction temperatures. At higher mole equivalent of THDB to 4-nitrophenol, it was anticipated that the reaction would follow a pseudo-first order based on 4-nitrophenol concentration [H. Wakayama, N. Setoyama, Y. Fukushima, Adv. Mater. 15 (2003) 742-745, incorporated herein by reference in its entirety]. Accordingly, the $ln(C_t/C_o)$ vs. reduction time showed a linear dependence (see FIGS. 14A-C). The rate constants (k) computed from respective slopes were determined to be: $9.4 \times 10^{-2}$, $1.5 \times 10^{-1}$, and $4.6 \times 10^{-1}$ mole $L^{-1}$ min$^{-1}$ at 40, 50, and 60° C., respectively. An apparent activation energy, which is an empirical parameter for all chemical reactions, was calculated on the basis of Arrhenius model. The plot demonstrates a linear relationship between the reduction of 4-nitrophenol and the value of apparent activation energy, which was calculated from the slope of the straight line. The apparent activation energy was found to be 8.3 kcal/mol [Y. Lu, Y. Mei, M. Drechsler, M. Ballauff, Angew. Chem. Int. Ed. 45 (2006) 813-816, incorporated herein by reference in its entirety].

TABLE 1

Rate constants of catalyst 1c at various temperatures

| Ser. No. | Temperature (° C.) | k value | Error limit |
|---|---|---|---|
| 1 | 40 | 9.4 × 10$^{-2}$ | 0.006 |
| 2 | 50 | 1.5 × 10$^{-1}$ | 0.017 |
| 3 | 60 | 4.6 × 10$^{-1}$ | 0.085 |

Having established the potential of Rh@Fe$_3$O$_4$ catalysts for nitrophenol reduction, their application was extended to a series of nitroarenes with structurally divergent functional group and the results are summarized in Table 2. For instance, 95% conversion of aniline was achieved in 10 min using catalyst 1b (Table 2, entry #7). Furthermore, in case of 1c, 80% of nitrobenzene is readily converted to its corresponding amine in 4 min; the conversion is complete in 6 min with exclusive selectivity (Table 2, entry #8-11), and the conversion at room temperature is complete within 1 h.

TABLE 2

Reduction of nitro-aromatics using Rh@Fe$_3$O$_4$ catalysts in water

| Entry | Catalyst | Substrate | Temp (° C.) | Time (min.) | Conv.$^a$ | Sel.$^b$ |
|---|---|---|---|---|---|---|
| 1 | 1a | R$_1$ = R$_2$ = R$_4$ = H; | 60 | 10 | >84 | 100 |
| 2 | 1b | R$_3$ = OH | 60 | 10 | >93 | 100 |
| 3 | 1c | | 40 | 25 | >99 | 100 |
| 4 | 1c | | 50 | 10 | 99 | 100 |
| 5 | 1c | | 60 | 5 | >99 | 100 |
| 6 | None | | 60 | 720 | <10 | Nd |
| 7 | 1b | R$_1$ = R$_2$ = R$_3$ = R$_4$ = H | 60 | 10 | 95 | 100 |
| 8 | 1c | R$_1$ = R$_2$ = R$_3$ = R$_4$ = H | 60 | 4 | 80 | 100 |
|  |  |  |  | 6 | 99 | 100 |
| 9$^c$ | 1c | R$_1$ = R$_2$ = R$_3$ = R$_4$ = H | Rt | 60 | >99 | 100 |
| 10$^c$ | None | R$_1$ = R$_2$ = R$_3$ = R$_4$ = H | Rt | 1440 | 14 | Nd |
| 11$^d$ | 1c | R$_1$ = R$_2$ = R$_3$ = R$_4$ = H | 60 | 1440 | No rxn | — |
| 12 | 1b | R$_1$ = OH; R$_2$ = R$_3$ = R$_4$ = H | 60 | 30 | 87 | 97 |
| 13 | 1c | R$_1$ = OH; R$_2$ = R$_3$ = R$_4$ = H | 60 | 30 | 90 | 95 |
| 14 | 1c | R$_1$ = Me; R$_2$ = R$_3$ = R$_4$ = H | 60 | 10 | 93 | 100 |
| 15 | 1b | R$_1$ = R$_3$ = R$_4$ = H; R$_2$ = Me | 60 | 10 | >95 | 100 |
| 16 | 1c | R$_1$ = R$_2$ = R$_4$ = H; R$_3$ = Me | 60 | 10 | 99 | 99 |
| 17 | 1c | R$_1$ = R$_2$ = R$_4$ = H; R$_3$ = Me | 60 | 10 | 99 | 98 |
| 18 | 1c | R$_1$ = R3 = R$_4$ = H; R$_2$ = NH$_2$ | 60 | 10 | >99 | 100 |
| 19 | 1c | R$_1$ = R$_2$ = R$_4$ = H; R$_3$ = OMe | 60 | 15 | 75 | 100 |
|  |  |  |  | 60 | 94 | 100 |
| 20 | 1b | R$_1$ = R$_2$ = R$_4$ = H; R$_3$ = Cl | 80 | 120 | 87 | 93 |
| 21 | 1c | R$_1$ = R$_2$ = R$_4$ = H; R$_3$ = Cl | 80 | 15 | 36 | 100 |
|  |  |  | 80 | 60 | 70 | 91 |
|  |  |  | 80 | 120 | 95 | 82 |
| 22 | 1c | R$_1$ = R$_4$ = Me; R$_2$ = R$_3$ = H | 80 | 150 | 36 | 100 |

$^a$from GC measurement;
$^b$identified by GCMS;
$^c$reaction carried out in 0.5 mmol of nitrobenzene in 5 mL water at room temperature;
$^d$without THDB.

The effect of functional group location on the aromatic ring was also examined. As seen from entry #13, o-nitrophenol had excellent selectivity but the conversion was limited to about 87%. But with catalyst 1c, conversion was improved with a comparable selectivity with 1b. Such lower conversion from p-nitrophenol (entry #5) could be attributed to its lower stability compared with p-nitrophenol, as a result of less effective resonance and impact of steric effect [K. Layek, M. L. Kantam, M. Shirai, D. Nishio-Hamane, T. Sasakid, H. Maheswaran, Green Chem. 14 (2012) 3164-3174, incorporated herein by reference in its entirety]. Furthermore, catalytic activity of ortho, meta, and para substituted nitrotoluene were evaluated (entries #14-17) and m-nitrotoluene was found to be the most reactive, as it was completely reduced to amine within 10 min. This could be due to a higher electron density on the nitrogen atom of the nitro group in the ortho and para position than on the meta location, which could cause hindrance toward overcoming the kinetic barrier. In addition, even though the positive inductive effect of methyl group on ortho and para analogs may be similar, the steric hindrance present in o-nitrotoluene makes it less stable [S. K. Maity, N. C. Pradhan, A. V. Patwardhan, App. Catal. A: 301 (2006)251-258, incorporated herein by reference in its entirety]. This explains the results obtained for the reduction of dimethylnitrobenzene (entry #22). The selectivity of halogen-substituted nitroarenes was also evaluated (entry #21) and the results illustrate that these substrates were quantitatively reduced to corresponding anilines with some amounts of dehalogenated products observed using catalyst 1c.

The greater activity of catalysts 1b and 1c over 1a can be explained on the basis of the uniform distribution of extremely tiny (<1 nm) Rh particles supported on magnetite surface, leading to a larger number of sub-nanosized particles per unit mass of $Fe_3O_4$. Thus, increased atom fraction, uniform distribution, high exposure and sub-nanometer size of Rh particles are relevant factors that make such catalysts highly reactive in this type of reactions. Furthermore, the strong interaction of nitrophenol with a large number of hydroxyl groups present on the Rh@$Fe_3O_4$ surface accelerates the rate of electron transfer process, as shown by Corma et al. [A. Corma, P. Concepcion, P. Serna, Angew. Chem. Int. Ed. 46 (2007) 7266-7269, incorporated herein by reference in its entirety] in the Au/$TiO_2$ system, and the subsequent fast desorption of 4-aminophenol from the surface enhances the reactivity of the surface sites.

Example 6

Reusability of Catalysts

The reusability of 1c catalyst has been studied at room temperature in aqueous medium using nitrobenzene as the substrate and following optimized reaction conditions. At the end of each reaction, the catalyst was extracted magnetically, washed repeatedly with water and ethyl acetate, and used again in the reduction of a fresh batch of nitrobenzene. The process was repeated successfully for up to 5 consecutive cycles without any significant loss of reactivity. The Rh content was determined after the 5th cycle and no sign of Rh leaching was detected in the ICP-OES study. The recycled catalyst was also examined by TEM (see FIGS. 15A-B). No surface deformation or aggregation of particles was detected.

Example 7

In summary, a heterogeneous catalytic system comprising sub-nanosized Rh on $Fe_3O_4$ nanoparticles has been developed, characterized, and applied for heterogeneous catalytic hydrogen transfer reactions. Rh/$Fe_3O_4$ demonstrated excellent reactivity on the reduction of a series of nitroarene compounds using tetrahydroxydiboron as a reductant in water in a short span of time. The reduction reaction proceeds without the formation of any nitrophenolate intermediates and proceeds directly from nitrophenol to aminophenol. The catalyst stability has been tested up to five consecutive cycles and was found to retain its original structure and morphology without significant leaching of Rh. Magnetic separation of the spent catalyst made it more convenient for re-use in multiple cycles.

Therefore, meritorious features of the present work include: superior and reproducible design of Rh particles with sizes in the sub-nano region which are deposited on $Fe_3O_4$, first time use of THDB as a hydrogen source for nitro compound reduction, higher reduction efficiency, catalyst stability after multiple cycles and recyclability. Furthermore, performing the reduction reaction in environmentally benign solvents such as water and stoichiometric use of THDB provide a new route for the reduction of nitro compounds.

The invention claimed is:

1. A supported catalyst, comprising:
   a support material comprising $Fe_3O_4$; and
   a catalytic material comprising rhodium disposed on the support material;
   wherein:
   the catalytic material is in the form of subnanoparticles having an average particle size of 0.2-0.99 nm;
   the rhodium is present in an amount of 1-20 wt % relative to a total weight of the supported catalyst; and
   the support material is devoid of $Al_2O_3$.

2. The supported catalyst of claim 1, wherein the $Fe_3O_4$ is in the form of nanospheres.

3. The supported catalyst of claim 2, wherein the nanospheres have an average particle size of 5-25 nm.

4. The supported catalyst of claim 1, wherein the rhodium is present in an amount of 4-10 wt % relative to a total weight of the supported catalyst.

5. The supported catalyst of claim 1, which has a BET surface area in a range of 100-180 $m^2/g$.

6. The supported catalyst of claim 1, which has a saturation magnetization value in a range of 50-75 emu/g.

7. The supported catalyst of claim 1, wherein the support material consists of $Fe_3O_4$.

8. A method of preparing the supported catalyst of claim 1, the method comprising:
   mixing the support material comprising $Fe_3O_4$ which is devoid of $Al_2O_3$ with a solution comprising a rhodium salt to form a suspension;
   heating the suspension to form a reaction mixture; and
   mixing ammonium hydroxide with the reaction mixture thereby forming the supported catalyst.

9. The method of claim 8, wherein the rhodium salt is rhodium(III) nitrate.

10. The method of claim 8, wherein the heating is carried out at a temperature of 50-120° C.

* * * * *